US005587459A

United States Patent [19]
Uckun

[11] Patent Number: 5,587,459
[45] Date of Patent: Dec. 24, 1996

[54] IMMUNOCONJUGATES COMPRISING TYROSINE KINASE INHIBITORS

[75] Inventor: Fatih M. Uckun, White Bear Lake, Minn.

[73] Assignee: Regents of the University of Minnesota, Minneapolis, Minn.

[21] Appl. No.: 293,731

[22] Filed: Aug. 19, 1994

[51] Int. Cl.$^6$ ............................................. C07K 16/28
[52] U.S. Cl. ................................. 530/391.1; 530/391.7; 530/391.9; 530/388.75
[58] Field of Search ........................... 530/391.1, 391.7, 530/391.9

[56] References Cited

U.S. PATENT DOCUMENTS

| | | |
|---|---|---|
| 4,831,117 | 5/1989 | Uckun . |
| 4,841,077 | 6/1989 | Ito et al. . |
| 4,960,908 | 10/1990 | Ito et al. . |
| 5,331,014 | 7/1994 | Kimura et al. . |

FOREIGN PATENT DOCUMENTS

| | | |
|---|---|---|
| 61-246124 | 11/1986 | Japan . |
| 3275625 | 12/1991 | Japan . |
| WO9323069 | 11/1993 | WIPO . |

OTHER PUBLICATIONS

Akiyama et al., "Genistein, A Specific Inhibitor of Tyrosine–Specific Protein Kinases", *J. Biol. Chem.*, 262, 5592 (1987).
Bolen et al., "Signal Transduction by the Src Family of Tyrosine Protein Kinases in Hematopoietic Cells", *Cell Growth and Differentiation*, 2, 409 (Aug. 1991).
Bolen et al., "The Src Family of Tyrosine Protein Kinases in Hematopoietic Signal Transduction", *Faseb J.*, 6, 3403 (1992).
Bolen et al., "Expression and Interactions of the Src Family of Tyrosine Protein Kinases in T Lymphocytes", *Adv. Can. Res.*, 57, 103 (1991).
Campbell et al., "Protein Tyrosine Phosphorylation is Induced in Murine B Lymphocytes in Response to Stimulation with Anti–Immunoglobulin", *Embo. J.*, 9, 2125 (1990).
Chae et al., "Role of Tyrosine Phosphorylation in Radiation–induced Activation of c–jun Protooncogene in Human Lymphohematopoietic Precursor Cells", *Cancer Research*, 53, 447 (Feb. 1, 1993).
Constantinou et al., "Induction of Differentiation and DNA Breakage in Human HL–60 and K–562 Leukemia Cells by Genistein (Meeting Abstract)", *Proc. Ann. Meet. Am. Assoc. Cancer Res.*, 31, A2605 (1990).
Constantinou et al., "Induction of Differentiation and DNA Strand Breakage in Human HL–60 and K–562 Leukemia Cells by Genistein", *Cancer Res.*, 50, 2618 (1990).
Honma et al., "Herbimycin A, an Inhibitor of Tyrosine Kinase, Prolongs Survival of Mice Inoculated with Myeloid Leukemia C1 Cells with High Expression of *v–abl*, Tyrosine Kinase", *Cancer Res.*, 52, 4017 (1992).

Hunter et al., "Protein Tyrosine Kinases", *Annu. Rev. Biochem.*, 54, 897 (1985).
Okabe et al., "Effects of Herbimycin A, an Antagonist of Tyrosine Kinase, on *bcr/abl* Oncoprotein–Associated Cell Proliferations: Abrogative Effect on the Transformation of Murine Hematopoietic Cells by Transfection of a Retroviral Vector Expressing Oncoprotein P210$^{bcr/abl}$ and Preferential Inhibition on Ph$^1$–Positive Leukemia Cell Growth", *Blood*, 80, 1330 (1992).
Okabe et al., "New Insight into Oncoprotein–Targeted Antitumor Effect: Herbimycin A as an Antagonist of Protein Tyrosine Kinase against Ph$^1$–Positive Leukemia Cells", *Leukemia and Lymphoma*, 12, 41 (1993).
Otani et al., "Tyrosine Kinase (s) regulate Apoptosis and bcl–2 Expression in a Growth Factor–Dependent Cell Line", *J. Biol. Chem.*, 268, 22733 (Oct. 21, 1993).
Peterson et al., "Genistein Inhibition of the Growth of Human Breast Cancer Cells: Independence from Estrogen Receptors and the Multi–Drug Resistance Gene", *Biochem. Biophys. Res. Com.*, 179, 661 (1991).
Schiven et al., "Reactive Oxygen Intermediates Activate NF–κB in a Tyrosine Kinase–Dependent Mechanism and in Combination with Vanadate Activate the $p56^{lck}$ and $p59^{fyn}$ Tyrosine Kinases in Human Lymphocytes", *Blood*, 82, 1212 (Aug. 15, 1993).
Spinozzi et al., "The Natural Tyrosine Kinase Inhibitor Genistein Produces Cell Cycle Arrest and Apoptosis in Jurkat T–Leukemia Cells", *Leuk. Res.*, 18, 431 (1994).
Takekura et al., "Effects of tyrosine kinase inhibitor, erbstatin, on cell growth and growth–factor/receptor gene expression in human gastric carcinoma cells", *Int. J. Cancer*, 47, 938 (1991).
Thomas, "New Horizons in Cancer Therapy", *Drugs of Today*, 28, 311 (1992).
Traganos et al., "Effects of Genistein on the Growth and Cell Cycle Progression of Normal Human Lymphocytes and Human Leukemic MOLT–4 and HL–60 Cells", *Cancer Res.*, 52, 6200 (1992).
Uckun et al., "Radiation Damage Repair Capacity of Primary Clonogenic Blasts in Acute Lymphoblastic Leukemia", *Cancer Research*, 53, 1431 (Mar. 15, 1993).
Uckun et al., "Signal Transduction Through the CD19 Receptor during Discrete Developmental Stages of Human B–cell Ontogeny", *The Journal of Biological Chemistry*, 268, 21172 (Oct. 5, 1993).

(List continued on next page.)

*Primary Examiner*—Lila Feisee
*Attorney, Agent, or Firm*—Merchant, Gould, Smith, Edell, Welter & Schmidt, P.A.

[57] ABSTRACT

Immunoconjugates effective for treating cancers and autoimmune diseases in humans are provided which comprise a tyrosine kinase inhibitor linked to a ligand targeting a cell surface receptor which are specifically capable of inhibiting receptor associated tyrosine kinases.

4 Claims, 21 Drawing Sheets

OTHER PUBLICATIONS

Uckun et al., "Ionizing-Radiation Stimulates Unidentified Tyrosine-Specific Protein Kinases in Human Lymphocyte-B Precursors, Triggering Apoptosis and Clonogenic Cell-Death", *PNAS USA*, 89, 9005 (Oct. 1992).

Uckun et al., "Tyrosine Phosphorylation is a Mandatory Proximal Step in Radiation-Induced Activation of the Protein Kinase C Signaling Pathway in Human B-Lymphocyte Precursors", *PNAS USA*, 90, 252 (Jan. 1993).

Waddick et al., "Engagement of the CD19 receptor on human B-lineage leukemia cells activates LCK tyrosine kinase and facilitates radiation-induced apoptosis", *Radiation Research*, 136, 313 (Dec. 27, 1993).

Yamanashi et al., "Association of B Cell Antigen Receptor with Protein Tyrosine Kinase Lyn", *Science*, 251, 192 (1991).

Canevari et al., Annals of Oncology, vol. 5, pp. 698–701, (1994).

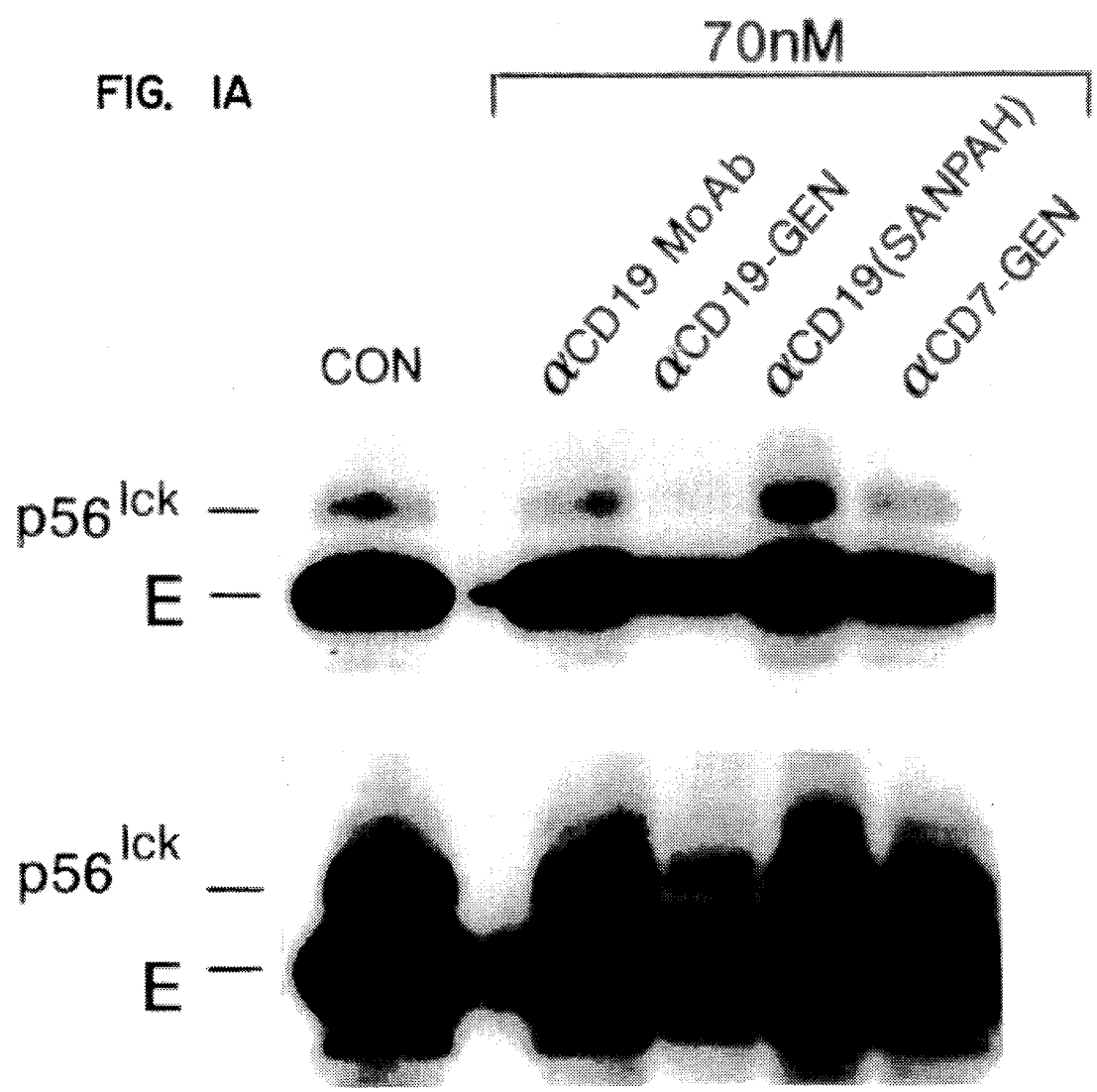

A.1 Kidney

B.1 Liver

C.1 Stomach

IMMUNOCONJUGATES COMPRISING TYROSINE KINASE INHIBITORS

BACKGROUND OF THE INVENTION

Cancer is the leading cause of death, second only to heart disease, of both men and women. In the fight against cancer, numerous techniques have been developed and are the subject of current research, directed to understanding the nature and cause of the disease, and to provide techniques for control or cure thereof.

Three major families of antitumor agents are known. Each of the families of agents is associated with a recognized mechanism of action. First, antitumor agents may be alkylating agents, which generally bind in a covalent manner with DNA to form bifunctional lesions. The bifunctional lesions involve adjacent or nearby bases of the same strand, or alternatively, involve bases on opposite strands forming interstrand crosslinks. Second, antitumor agents may be antimetabolites, which generally inhibit enzymes involved in the synthesis or assembly of DNA. Alternatively, an antimetabolite may serve as a fraudulent or analog substrate of DNA processes. Third, antitumor agents may be antibiotics, which work by intercalating into the DNA helix or introducing strand breaks into DNA.

Thousands of potential anticancer agents have been evaluated. Essentially, all effective agents (of which very few have been found) appear to work by one of the above-mentioned mechanisms.

Drug targeting is a potentially attractive new approach to killing malignant cells, which leaves normal tissue unharmed. A decisive breakthrough in drug targeting was the advent of hybridoma technology, making monoclonal antibodies (MoAb) available in limitless supply. To construct reagents with selectivity for certain populations of tumor cells, MoAbs or other cell targeting proteins are linked to bioactive agents to form immunoconjugates which combine the selectivity of the carrier moiety with the potency of the bioactive moiety. The choice of monoclonal antibody is based on the surface antigen profile of a malignant cell as determined by analysis of clonogenic blasts.

For the past decade, immunoconjugates have been under investigation for the treatment of various cancers, and more recently for the treatment of immunological disorders such as rheumatoid arthritis and acquired immune deficiency syndrome (AIDS). Although these agents have shown some potential to provide safe and effective therapy for human disease, many difficulties remain. Ideally, consistently locatable and reliable markers on target cells would permit the binding portion of immunoconjugates to completely avoid non-target tissue. In reality, cross-reactivity with antigens expressed by vital life-maintaining organs often gives rise to unacceptable complications in in vivo applications. There is also the potential that patients will demonstrate immune responses to the separate components of the immunoconjugates even though they may already be immunosuppressed by the course of their disease. Moreover, the cytotoxicity obtained in in vitro studies may be limited in clinical application due to a lack of potency in doses that can be tolerated by the patient. Finally, solid tumors are difficult to penetrate thoroughly and in hematologic malignancies, residual disease can cause relapse despite easier access to target cells in leukemias and lymphomas.

Thus, there are serious and recurring problems with immunoconjugate therapy. Therefore, there is continuing need for improved agents and methods of their use to target and inhibit or eliminate cell populations associated with various pathologies.

SUMMARY OF THE INVENTION

The present invention provides an immunoconjugate comprising a tyrosine kinase (TK) inhibitor linked to a cell specific protein ligand such as an antibody which binds to a cell surface receptor associated with tyrosine kinase activity, such as a receptor which forms a complex with an Src protooncogene family protein tyrosine kinase. The tyrosine kinase inhibitor acts to inhibit the receptor-associated tyrosine kinase, and to inhibit or kill the target cell, without affecting other cellular tyrosine kinases.

The present invention is based upon our finding that a number of cell surface receptors that lack an intracellular catalytic domain associate with Src protooncogene family protein tyrosine kinases (PTKs) to form cell-type specific transmembrane receptor tyrosine kinases with ancillary signal transducing functions. Src family PTKs in such receptor-PTK complexes act as signal transducers and couple the receptor to downstream cytoplasmic signaling pathways. Therefore, such cell-type specific transmembrane receptor kinases are suitable targets for biotherapy using PTK inhibitors, since they can be targeted via antibodies specific to their associated receptor. For example, Lyn kinase, which is associated with the CD19 receptor in a number of cancer cells is readily inhibited by an immunoconjugate comprising an anti-CD19 monoclonal antibody, while Syk kinase, which is not associated with CD19, is not. Furthermore, a given kinase is inhibited in a human cancer cell only if the cancer cell expresses its associated receptor, i.e., Lyn is not inhibited in the absence of CD19.

Thus, a preferred embodiment of the invention comprises a TK inhibitor such as an isoflavone, linked to a monoclonal antibody, which binds to a receptor on a cancer cell. Preferred monoclonal antibody/receptor combinations include B43/anti-CD19, B53/anti-CD4, BXU/anti-Bp47, TXU-1/anti-Tp 120, NXU/antineuroblastoma, TP3/anti-osteosarcoma. Preferred antibodies are specifically reactive with the surface of human cancer cells (more specifically, B-lineage acute lymphoblastic leukemia cells and lymphoma cells for B43 and anti-BP47; T-lineage leukemia and lymphoma cells for B53 and TXU-1; neuroblastoma cells for NXU; and osteosarcoma cells for TP3). As used herein, the term "antibody" includes cell-specific antibody fragments and subunits thereof.

The tyrosine kinase inhibitors of the present immunoconjugates unexpectedly induce apoptotic death in target cells. This is in contrast to the previously reported activity of tyrosine kinase inhibitors such as genistein, which have been reported to block radiation-induced apoptosis. Furthermore, daidzein, which had previously been reported not to possess TK inhibitory activity, exhibits effective levels of anti-TK activity when linked to cell targeting molecules to yield one of the immunoconjugates of the present invention.

For example, immunoconjugates comprising genistein induce apoptosis in radiation resistant and multidrug resistant tumor cells expressing high amounts of BCL2 protein. Normally, BCL2 protein prevents the cytotoxic action of all known drugs and radiation but does not appear to inhibit the action of immunoconjugates containing genistein. Furthermore, as demonstrated by the examples hereinbelow, the present immunoconjugates kill in vitro the clonogenic fraction of target tumor cells, are able to penetrate multiple organs in the SCID mouse model and selectively accumulate in those organs infiltrated with human tumor cells, kill in vivo, in a surrogate model of human leukemia, therapy refractory human leukemia cells without any toxicity to the treated animal, are superior to antibodies or TK inhibitors used singly, and are superior to all other drugs which were tested in the model systems.

Therefore, the present invention also provides a method to inhibit TK activity in populations of cells having cell surface receptors associated with TK activity, as discussed above, and in detail below. The preselected cell population is contacted either in vivo or in vitro with an immunoconjugate of the invention, in a amount effective to inhibit the TK activity, and thus, the cellular events associated with TK activity, in said population. It is expected that the immunoconjugate of the present invention will be effective in the treatment of diseases or pathologies associated with the proliferation of undesirable mammalian cells such as B-cells, NK cells and T-cells, either alone or in combination with immunotoxins or with conventional therapies for such afflictions. Such pathologies include other cancers, such as acute lymphoblastic leukemia, B-cell lymphoma, Burkitt's lymphoma; carcinomas such as lung, breast, colon, or ovarian cancer; epidermoid cancers; cancers of the CNS or other leukemias. The immunoconjugates of the present invention may also be useful as immunosuppressive agents to suppress T-cell proliferation associated with organ rejection or NK cells involved in rejection of bone marrow transplants or to treat autoimmune diseases including, but not limited to, systemic lupus erythematosus, rheumatoid arthritis, nonglomerular nephrosis, psoriasis, chronic active hepatitis, ulcerative colitis, Crohn's disease, Behçet's disease, chronic glomerulonephritis (membranous), chronic thrombocytopenic purpura, allograft rejection and autoimmune hemolytic anemia.

BRIEF DESCRIPTION OF THE DRAWINGS

FIG. 1[B] depicts the results of an immunoblotting assay which show that the treatment of RAMOS lymphoma cells with B43-GEN decreases tyrosine phosphorylation of abundant protein substrates.

FIG. 1[C] is an immunoblot demonstrating that B43-GEN is substantially more effective than unconjugated GEN in inhibiting the LYN kinase in B-lineage leukemia cells. The immunoblot further demonstrates that TXU(anti-CD7)-GEN (used as a control) does not inhibit LYN kinase, providing evidence that the B43-GEN induced LYN inhibition is CD19 receptor specific.

FIG. 1[D] is an immunoblot demonstrating that B43-GEN is substantially more effective than unconjugated GEN in decreasing tyrosine phosphorylation of abundant phosphoprotein substrates in B-lineage leukemia cells. The immunoblot further shows that this effect is CD19 receptor specific since an anti-CD7-GEN does not decrease tyrosine phosphorylation.

FIG. 1[E] depicts the results of an immunoblotting assay which show that treatment of B-lineage leukemia cells with B43-GEN immunoconjugate inhibits LYN kinase which is associated with the CD19 receptor, whereas unconjugated B43 antibody, SANPAH modified B43 antibody and the control immunoconjugate anti-CD7-GEN do not.

FIG. 1[F] depicts the results of an immunoblotting assay which show that treatment of B-lineage ALL cells with B43-GEN immunoconjugate does not inhibit SYK tyrosine kinase which is not associated with the CD19 receptor.

FIG. 1[G] depicts the results of a serine kinase renaturation assay which show that treatment of B-lineage leukemia cells with B43-GEN immunoconjugate does not inhibit PKC or PKC dependent renaturable serine kinases.

FIG. 2[A] depicts Wright Giemsa stained cytospin slides which illustrate the morphologic features of B43-GEN treated leukemia cells undergoing apoptosis.

FIG. 6[B] is a depiction of the activity of B43-GEN against human B-lineage lymphoma in SCID mice. The probability of event-free survival was determined and event-free interval curves were generated using the Kaplan-Meier product limit method.

FIG. 7[B] is a depiction of the plasma concentrations vs time curves for B43-GEN following i.v. injection of 71 pmol into SCID mice with end-stage human B-lineage leukemia (-□-) or 58 pmol injected i.v. to healthy SCID mice which have not been inoculated with leukemia cells (-o-). Lines represent two-compartment model simulations, symbols depict measured concentrations.

FIG. 7[C] is a depiction of the plasma or tissue concentrations vs. time curves after i.v. injection of 58 pmol GEN (Δ) or BP43-GEN (o,) into SCID mice with end stage leukemia (dashed lines) or no leukemia (solid lines). Lines represent simulations from the physiological pharmacokinetic model, symbols depict measured concentrations.

DETAILED DESCRIPTION OF THE INVENTION

1. Protein Tyrosine Kinases

Figure 1B:
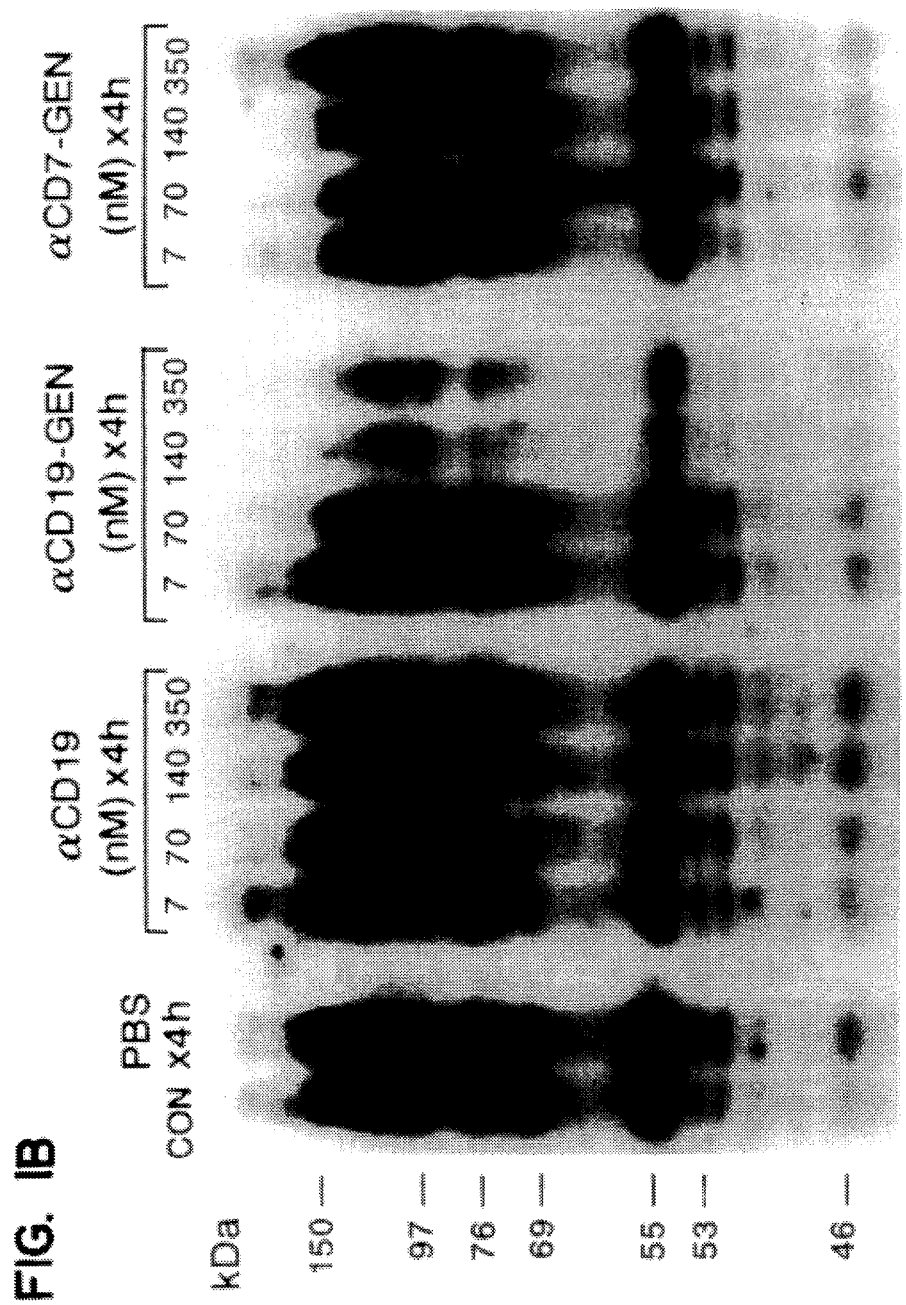
FIG. 1[A] depicts an immunoblot demonstrating that the treatment of RAMOS lymphoma cells with B43-GEN inhibits CD19-associated LCK kinase. The lower part of the figure represents a longer exposure time.

Cell growth is controlled, to a large degree, by extracellular ligands which bind to specific receptors on the surface of cells. Cross et al., *Cell*, 64, 2171 (1991). A number of these receptors, including the EGF receptor, have intrinsic protein tyrosine kinase (PTK) activity. Yarden et al., *Ann. Rev. Biochem.*, 57, 443 (1988). Ligand-dependent activation of receptor associated TKs or unregulated synthesis of TK oncoproteins results in tyrosine phosphorylation of cellular substrates which have a critical role in the control of mitogenesis, cell cycle regulation, cell survival and cellular transformation. Ullrich et al., *Cell*, 61, 203 (1990).

Among the cellular enzymes that are involved in signal transduction, the protein tyrosine kinases (PTKs) appear to play key roles in the initiation of various signaling cascades. PTKs can be divided into two major groups on the basis of their predicted structures. The first PTK group, which contains those that possess extracellular domains which generally function to bind peptide hormones, are the receptor PTKs. Examples of PTKs included in this group are the receptors for epidermal growth factor, the nerve growth factor and platelet-derived growth factor.

The second PTK group contains those that lack the extracellular domains and are categorized as the nonreceptor PTKs, even though many members of this group appear to be associated, albeit noncovalently, with some type of cell surface ligand-binding protein. Members of this group include the Src family of PTKs as well as the members of the fes/fps and abl gene families. The nonreceptor class of PTKs is growing with regard to the number of enzymes it includes and is also demonstrating surprising diversity in predicted structure.

TABLE 1

PTK/Surface Protein Associations

| Surface Protein | Src Family Member |
|---|---|
| CD2 | Lck |
| CD4 | Lck |
| CD8 | Lck |
| CD28 (FcεRII) | Fyn |
| CD28 | Lck, Fyn |
| CD32 (FcγRII) | Src |
| CD36 | Fyn, Lck, Yes |
| CD48 | Lck |
| CD55 | Lck |
| CD59 | Lck |
| Thy-1 | Lck, Fyn |
| TCR (δ or CD8) | Fyn |
| IL-2β | Lck, Fyn, Lyn |
| sIgM | Blk, Lyn, Fyn, Hck, Lck |
| sIgD | Blk, Lyn, Fyn, Hck, Lck |
| FcεRI | Lyn, Src, Yes |
| IL-8R | Lyn |
| GM-CSFR | Lyn, Yes |

The Src family of nonreceptor PTK enzymes currently contains nine members: Src, Yes, Fyn, Lyn, Lck, Hck, Fgr, Blk, and Yrk. The Src, Yes, Fyn, and Lyn proteins are expressed in a variety of cell types, whereas the Lck, Hck, Fgr and Blk proteins are expressed primarily in different types of hematopoietic cells. The distribution of Src PTKs in selected hematopoietic cells is shown in Table 2. Immediately obvious is the fact that in each cell type, multiple members of the Src family are usually present. It is also clear that some Src PTKs demonstrate significant restrictions with regard to the type of hematopoietic cell in which they are expressed. The Lck protein is found in thymocytes and mature T cells and has been reported to be expressed in mature mouse splenic B cells. Campbell et al., *Mol. Cell. Biol.*, 12, 2315 (1992). Additionally, Src is expressed by the cells associated with colon cancer, breast cancer and ovarian cancer as well as virtually all other forms of human cancer. Likewise, Fyn and Lyn are expressed in virtually all forms of human cancer.

TABLE 2

Distribution of Src Protein Tyrosine Kinases in Hematopoietic Cells

| Src Family Member | Molecular Wt. (kD) | Cell Type | | | | | | |
|---|---|---|---|---|---|---|---|---|
| | | T Cell | B Cell | NK Cell | Mast Cell | Monocyte | Granulocyte | Platelets |
| Src | 60–61 | −[a] | − | + | + | + | ? | + |
| Fyn | 59–60 | + | + | + | − | + | ? | + |
| Yes | 62 | + | − | + | + | ? | ? | + |
| Lyn | 55–58 | −[a] | + | + | + | + | ? | + |
| Lck | 56 | + | +/−[b] | + | − | − | − | − |
| Blk | 55–56 | − | + | − | − | − | − | − |
| Hck | 59–64 | − | + | − | + | + | + | + |
| Fgr | 58 | − | −[a] | − | − | + | + | − |

[a]Present in transformed or immortalized cells but not found routinely in normal cells.
[b]Presence detected in normal cells by some investigators, but not others.

The association of Src PTKs with surface proteins (antigens) in hematopoietic cells is summarized in Table 1, below.

Oncogenic transformation or immortalization of lymphocytes alters the pattern of expression of selected Src family members. For example, Lyn is expressed in T cells transformed by HTLV-I or herpesvirus saimiri (Yamanashi et al., *Proc. Natl. Acad. Sci. USA*, 86, 6538 (1991)) and Lck is expressed in immortalized and transformed B cells. Campbell et al., cited supra.

Moreover, signal transduction initiated through B-lymphocyte antigen receptors involves the activation of PTKs. Campbell et al., *EMBO. J.*, 9, 2125 (1990). Support for this view was initially provided by the observation that Lyn could be coimmunoprecipitated with sIgM from lysates from the murine B cell line WEHI-231. Yamanashi et al., *Science*, 251, 192 (1991).

Furthermore, tyrosine-specific protein kinase activity is known to be associated with oncogene products of the retroviral Src gene family. Hunter et al., *Annu. Rev. Biochem.*, 54, 897 (1985). This kinase activity is strongly correlated with the ability of retroviruses to transform cells, since mutants with reduced kinase activity have lower transforming efficiency, and mutants which lack tyrosine kinase activity are transformation defective. Bishop, *Annu. Rev. Biochem.*, 52, 301 (1983). Similar kinase activity is also associated with the cellular receptors for several growth factors such as EGF, platelet derived growth factor, insulin, and insulin like growth factor I. Ushiro et al., *J. Biol. Chem.*, 255 8363 (1980); Ek et al., *Nature*, 295 419 (1982); Kasuga et al., *Nature*, 298, 667 (1982); Jacobs et al., *J. Biol Chem.*, 258, 9581 (1983). Therefore, it is possible that tyrosine phosphorylation plays an important role for cell proliferation and cell transformation.

2. Protein Tyrosine Kinase Inhibitors

Several compounds have been reported to inhibit tyrosine kinase activity. For example, a protease inhibitor $N^\beta$-tosyl-L-lysyl chromomethyl ketone was demonstrated to inhibit tyrosine kinase activity associated with $pp60^{v-arc}$ and revert the effects of avian sarcoma virus transformation on cell morphology, adhesion, and glucose transport. Richert et al., *Cell*, 18, 369 (1979). Also, a flavone quercetin was reported to inhibit the tyrosine kinase activity of $pp60^{v-arc}$ as well as the activities of cAMP-independent protein kinase, the $Ca^{2+}$/phospholipid-dependent enzyme protein kinase C, phosphorylase kinase, $Na^+$, $K^+$-ATPase, and $Ca^{2+}$, $Mg^{2+}$-ATPase. Graziani et al., *Eur. J. Biochem.*, 135, 583 (1983); Graziani et al., *Biochim. Biophys. Acta*, 714, 415 (1981); Gschwendt et al., *Biochem. Biophys. Res. Commun.*, 124, 63 (1984); Srirastava et al., *Biochem. Biophys. Res. Commun.*, 131, 1 (1985); Lang et al., *Biochim. Biophys. Acta*, 333, 180 (1974); Shoshan et al., *J. Biol. Chem.*, 256, 887 (1981). Tyrphostins, derivative synthetics of erbstatin, which are a prototype of tyrosine analogue, have been reported to block phosphorylation of tyrosine residue and inhibit EGF dependent cell proliferation at concentrations showing little toxicity. Yaish et al., *Science*, 242, 933 (1988). Additionally, several flavonoid analogues have been disclosed to exhibit PTK inhibitory activities. Cushman, *J. Med. Chem.*, 34, 798 (1991). Furthermore, amiloride, which is well known as an inhibitor for $Na^+$, $K^+$ antiporter was shown to directly inhibit growth factor receptor tyrosine kinase activity. Davis et al., *J. Biol. Chem.*, 260, 2543 (1985). More recently, herbimycin A, although ineffective in reducing cAMP-dependent protein kinase or protein kinase C activity, was shown to inactivate various cytoplasmic tyrosine kinases, thereby indicating that the agent is a specific inhibitor of cytoplasmic PTKs. Fukuzawa et al., *Biochem. Pharmacol.*, 42, 1661 (1991).

a. Genistein

Genistein (GEN), an isoflavone (5,7,4'-trihydroxyisoflavone) derived from the fermentation broth of Pseudomonas spp, is a naturally occurring, specific tyrosine kinase inhibitor present in soybeans, soymeal and tofu. Akiyama et al., *J. Biol. Chem.*, 262, 5592 (1987). Genistein and related isoflavonoids are efficiently absorbed from the gastrointestinal tract and reach measurable levels in the plasma and urine and also have estrogenic activity. Adlercreutz et al., *Lancet.*, 342, 1209 (1993).

Genistein is a fairly specific inhibitor for tyrosine kinases, while it scarcely inhibits the activity of serine and threonine kinases. Ogawara et al., *J. Antibiot. (Tokyo)*, 39, 606 (1986). Furthermore, it inhibits topoisomerase I and II activity in ras-transformed NIH 3T3 cells. Okura et al., *Biochem. Biophys. Res. Commun.*, 157, 183 (1988).

Genistein has also been shown to be capable of preventing apoptosis in cells which have undergone ionizing radiation or engagement of the CD19 receptor. Uckun et al., *Proc. Natl. Acad. Sci. USA*, 89, 9005 (1992). Since activation of protein tyrosine kinases is a mandatory step in both instances, this inhibition occurs primarily through genistein's PTK inhibitory properties on all PTKs in the cell including those important for induction of cell death. Therefore, the immunoconjugates of the present invention can be said to provide an unexpected result—the induction of apoptosis in the targeted cell by inhibiting only those tyrosine kinases which are associated with a surface receptor and are important for cell survival. (See Example 6).

b. Apoptosis

Apoptosis is an active process requiring new protein synthesis. Typically, the process requires ATP, involves new RNA and protein synthesis, and culminates in the activation of endogenous endonucleases that degrade the DNA of the cell, thereby destroying the genetic template required for cellular homeostasis. Apoptosis is observed in controlled deletion of cells during metamorphosis, differentiation and general cell turnover and appears normally to be regulated by receptor-coupled events. For these reasons, apoptosis has been called "programmed cell death" or "cell suicide." Although every cell has this genetic program to commit suicide, it is usually suppressed. Under normal circumstances, only those cells no longer required by an organism activate this program.

Apoptotic cell death is characterized by plasma membrane blebbing, cell volume loss, nuclear condensation, and endonucleolytic degradation of DNA at nucleosome intervals. Loss of plasma membrane integrity is a relatively late event in apoptosis, unlike the form of cell death termed necrosis, which can be caused by hypoxia and exposure to certain toxins and which typically is characterized early-on by increased membrane permeability, cell, and rupture.

3. Cell specific protein ligands a. Monoclonal Antibodies

Monoclonal antibodies (MoAbs) are produced by the fusion of spleen lymphocytes with malignant cells (myelomas) of bone marrow primary tumors. Milstein, *Sci. Am.*, 243, 66 (1980). The procedure yields a hybrid cell line, arising from a single fused cell hybrid, or clone, which possesses characteristics of both the lymphocytes and myeloma cell lines. Like the lymphocytes (taken from animals primed with sheep red blood cells as antigens), the fused hybrids or hybridomas secrete antibodies (immunoglobulins) reactive with the antigen. Moreover, like the myeloma cell lines, the hybrid cell lines are immortal. Specifically, whereas antisera derived from vaccinated animals are variable mixtures of antibodies which cannot be identically reproduced, the single-type of immunoglobulin secreted by a hybridoma is specific to one and only one determinant on the antigen, a complex molecule having a multiplicity of antigenic molecular substructures, or determinants (epitopes). Hence, monoclonal antibodies raised against a single antigen may be distinct from each other depending on the determinant that induced their formation. However, all of the antibodies produced by a given clone are identical. Furthermore, hybridoma cell lines can be reproduced indefinitely, are easily propagated in vitro and in vivo, and yield monoclonal antibodies in extremely high concentration.

B43 is a murine IgG1, κ monoclonal antibody (MoAb) recognizing a 95 kDa target B lineage restricted phosphoglycoprotein, which is identified as the CD19 antigen according to the World Health Organization (WHO) established CD (cluster of differentiation) nomenclature. The chemical, immunological and biological features of B43 MoAb have been described in detail in previously published reports. Uckun et al., *Blood*, 71, 13 (1988). B43 is available from the American Type Culture Collection (ATCC), 12301 Parklawn Dr, Rockville, Md. 20852 deposited on Sep. 11, 1985, under designation number HB 8903. Chimeric and single chain Fv fragments of B43 have also been developed and should prove effective as B43-GEN immunoconjugates.

Other monoclonal antibodies useful in the practice of the present invention include, but are not limited to, B53/TXU-5, TXU-1, BXU/anti-Bp47, NXU and TP3. B53/TXU-5 is a murine IgG1 monoclonal antibody recognizing CD4 antigen on T helper cells and childhood T-cell leukemia cells. CD4 is associated with the LCK kinase and B53-GEN effectively inactivates LCK kinase leading to apoptotic death of target cells. TXU-1 is a murine IgG1 monoclonal antibody recognizing a 120 kDa novel antigen on normal and leukemic T-cells as well as NK cells; the target antigen is associated with LCK and FYN tyrosine kinases. BXU/anti-Bp47 is a murine IgG1 monoclonal antibody recognizing a 47 kDa novel antigen on B-lineage lymphoid cells; the target antigen is associated with BTK and LYN tyrosine kinases; anti-Bp47-GEN kills B-lineage leukemia and lymphoma cells in vitro and also in SCID mice, but is not as effective as B43-GEN. NXU is a murine IgG1 monoclonal antibody recognizing a 30 kDa novel antigen on neuroblastoma cells (neuroblastoma is the most common solid organ malignancy in children); the target antigen is associated with SRC and FYN tyrosine kinases. NXU-GEN kills neuroblastoma cells. TP3 is a murine IgG2a monoclonal antibody which recognizes a 80 kDa antigen on human osteosarcoma cells. This antigen is associated with FYN and SRC kinases.

The above antibodies or active fragments thereof, either chemically produced (Fab or Fab2 fragments) or genetically engineered (single chain Fv fragments), chimeric or humanized, when coupled to GEN, are expected to be effective to kill the cells which they target.

b. Cytokines

Additionally, cytokines can also be used for delivering genistein to their surface receptors. They also contain functional groups that allow them to be linked efficiently to genistein and other TK inhibitors. Furthermore, cytokine-genistein conjugates may even be more effective since they react with surface receptors that themselves have intrinsic tyrosine kinase activity (such as epidermal growth factor (EGF-kinase) and platelet derived growth factor (PDGF-R kinase)).

4. Immunoconjugates

Immunoconjugates (antibody-therapeutic agent conjugates) are a relatively new class of immunopharmacologic agents that are prepared by covalently linking cell type-specific polyclonal or monoclonal antibodies to a variety of bioactive agents or detectable labels either directly or via a linking agent.

5. Receptors on human lymphoid cells that form associations with tyrosine kinases A number of cell-surface receptors that lack an intracellular catalytic domain associate with Src family PTKs to form cell-type specific transmembrane receptor tyrosine kinases with ancillary signal transducing functions. The Src family PTK in such receptor-PTK complexes acts as a signal transducer and couples the receptor to downstream cytoplasmic signaling pathways. Examples for such associations include (a) the association of LCK with CD2, CD4, CD8, CD28, CD48, CD55, CD59, and IL-2 receptor β in T-lineage lymphoid cells, (b) the association of LYN with IL-2 receptor β, CD19, CD22, BP47, sIgM, and sIgD in B-lineage lymphoid cells, and (c) the association of FYN with CD23 and sIgM/sIgD in B-lineage lymphoid cells as well as with CD3, CD28, Thy-1, IL-7 receptor and IL-2 receptor il in T-lineage lymphoid cells. Thus, antibodies specific for these cell-surface antigens would be suitable vehicles for PTK inhibitors, thus delivering the inhibitors to the tyrosine kinases when the PTKs are in association with the cell-surface receptors.

Furthermore, epidermal growth factor receptor (EGF-R) and platelet derived growth factor receptor (PDGF-R) are expressed on various forms of human cancer including breast cancer, colon cancer and ovarian cancer, while nerve growth factor receptor (NGF-R) is expressed on brain tumors. Therefore, antibodies specific for these cell surface receptors would also be suitable vehicles for PTK inhibitors, thus delivering the inhibitors to the tyrosine kinases when in association with these cell surface receptors.

a. The CD19 surface antigen

CD19 antigen is a B-lineage specific surface receptor which is expressed on malignant cells from 85% of patients with acute lymphoblastic leukemia (ALL). Uckun et al., *Blood*, 71, 13 (1988). CD19 is found on the surface of each B-lineage lymphoma cell and B-lineage cell at a high density (>1,000,000 molecules/cell and >50,000 molecules/cell, respectively) but is absent from the parenchymal cells of life-maintaining nonhematopoietic organs, as well as from blood related myeloid and erythroid cells, T-cells and bone marrow stem cells, reducing the opportunity for nonspecific toxicity when anti-CD19 antibodies are used in biotherapy. Uckun et al., *J. Exp. Med.* 163, 347 (1986). This B-lineage specific antigen shows a high affinity for the B43 (anti-CD19) monoclonal antibody ($Ka>10^8 M^{-1}$), undergoes antibody induced internalization upon binding of B43 and is not shed from the cell surface. Uckun et al., *J. Exp. Med.* 163, 347 (1986). CD19$^+$ acute lymphoblastic leukemias are believed to originate from putative developmental lesions in normal B-cell precursor clones during early phases of ontogeny and are therefore classified as B-lineage leukemia F. M. Uckun, *Blood*, 76, 1908 (1990).

As noted above, CD19 physically and functionally associates with the Src protooncogene family protein tyrosine kinase LYN to form a cell-type specific transmembrane receptor tyrosine kinase with ancillary signal transducing functions. Uckun et al., *J. Biol. Chem.*, 268, 21172 (1993). In this complex, LYN acts as a signal transducer and couples CD19 to downstream cytoplasmic signaling pathways. Uckun et al., *J. Biol. Chem.*, 268, 21172 (1993). Since LYN is abundantly expressed in B-lineage leukemia cells, the CD19 receptor is a suitable target for biotherapy using PTK inhibitors. Bolen et al., *Adv. Can. Res.*, 57, 103 (1991).

6. Production and Purification of Immunoconjugates

Preferred immunoconjugates are formed by linking an effective cytotoxic amount of GEN molecules to each molecule of B43. For example, a reagent useful in the practice of the invention is an about 1:1 mixture of B43-GEN having one GEN molecule per B43 molecule.

Figure 10:
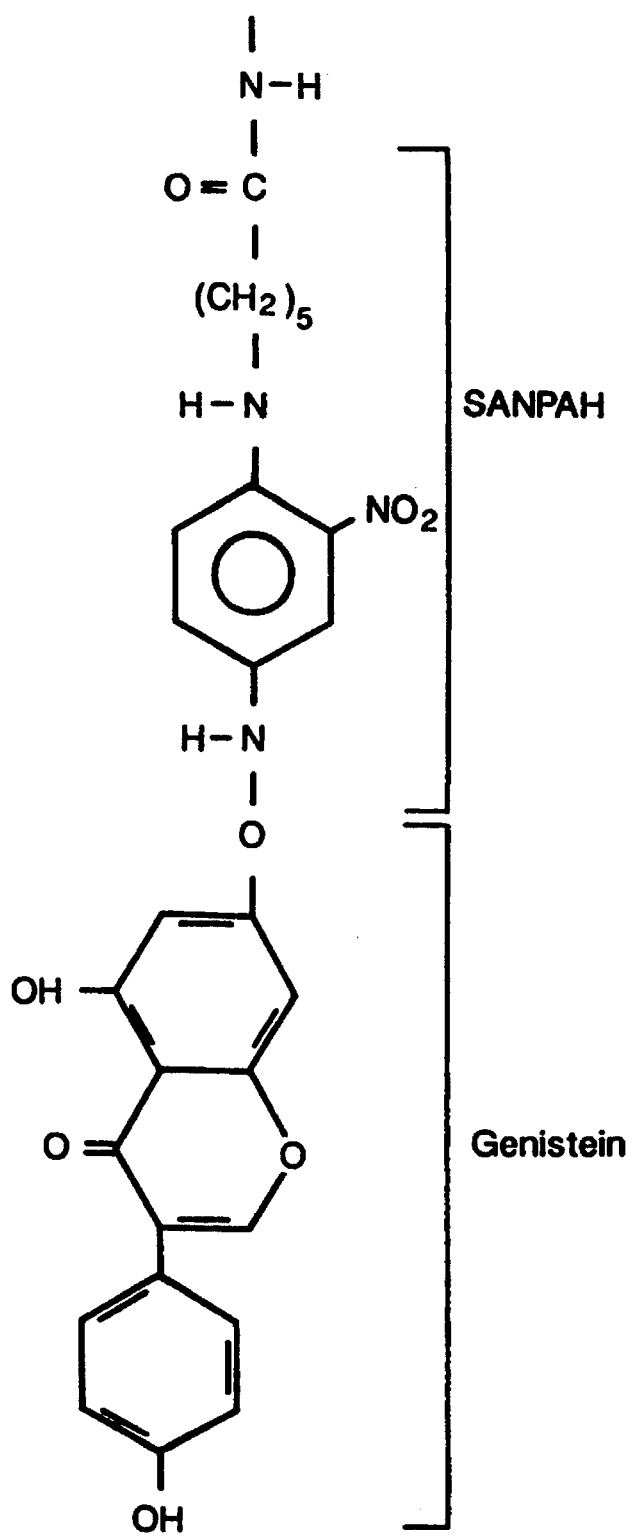
FIG. 10 shows the structure of B43-GEN.

Heterobifunctional azido-containing cross-linking reagents useful in the formation of monoclonal antibody- PTK inhibitor conjugates include sulfo-SADP (Sulfosuccinimidyl-(4-azidophenyldithio)propionate, cleavable by thiols and reducing agents) and sulfo-SANPAH (sulfosuccinimidyl-6-(4'-azido-2'-nitrophenylamino)hexanoate, noncleavable, extended chain length cross-linker). The azo groups link to proteins via NH bonds under photolytic conditions, e.g., 265–275 nm (Nz) or 300–460 nm (azonitrophenyl). For example, the particular B43-GEN employed in the examples hereinbelow is prepared by modifying B43 MoAb with the crosslinking agent sulfo-SANPAH and then reacting the modified B43 with a 25:1 molar excess of GEN. See FIG. 10. Similarly, sulfo-SADP (Sulfosuccinimidyl-(4-azidophenyldithio)propionate has been REACTI-VIALS to prepare B43-GEN as well as anti-Bp47-GEN immunoconjugates and it can be used for other GEN immunoconjugates as well.

Furthermore, although monoclonal antibodies cannot be linked directly to isoflavones using other crosslinking agents (besides sulfo-SANPAH) commonly known to those skilled in the art, isoflavones can be modified to produce aminoisoflavones which can be linked to monoclonal antibodies using such common crosslinking agents, i.e., N-succinimidyl 3-(2-pyridyldithio)propionate (SPDP), 4-succinimidyloxycarbonyl-methyl-(2-pyridyldithio)-toluene (SMPT) and N-succimidyl 6-[3-(2-pyridyldithio)propionamido]hexanoate (LC-SPDP).

7. Modes of Administration of the Immunoconjugate

The immunoconjugates of the present invention can be formulated as pharmaceutical compositions and administered to a mammalian host, such as a human patient, in a variety of forms adapted to the chosen route of administration, i.e., orally or parenterally, by intravenous, intramuscular or subcutaneous routes.

a. Dosage Forms

It is preferred that the immunoconjugate of the present invention be parenterally administered, i.e., intravenously or intraperitoneally by infusion or injection. Solutions or suspensions of the immunoconjugate can be prepared in water, or isotonic saline, such as PBS, optionally mixed with a nontoxic surfactant. Dispersions can also be prepared in glycerol, liquid polyethylene glycols, DMA, vegetable oils, triacetin, and mixtures thereof. Under ordinary conditions of storage and use, these preparations may contain a preservative to prevent the growth of microorganisms.

The pharmaceutical dosage form suitable for injection or infusion use can include sterile aqueous solutions or dispersions or sterile powders comprising the active ingredient which are adapted for the extemporaneous preparation of sterile injectable or infusible solutions or dispersions. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, and liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersion or by the use of nontoxic surfactants. The prevention of the action of microorganisms can be accomplished by various antibacterial and antifungal agents, for example, parabens, chlorobutanol, phenol, sorbic acid, thimerosal, and the like. In many cases, it will be desirable to include isotonic agents, for example, sugars, buffers or sodium chloride. Prolonged absorption of the injectable compositions can be brought about by the inclusion in the compositions of agents delaying absorption, for example, aluminum monostearate hydrogels and gelatin.

Sterile injectable solutions are prepared by incorporating the immunoconjugates in the required amount in the appropriate solvent with various of the other ingredients enumerated above, and as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

b. Dosages

The concentration of the immunoconjugate in said composition can be varied widely, in accord with the size, age and condition of the patient. Useful dosages of the immunoconjugates can be determined by comparing their in vitro activity, and in vivo activity in animal models, to that of an equivalent dosage of cyclophosphamide. For example, an immunoconjugate of the present invention that is 10–20 times more potent than cyclophosphamide against a particular cancer may be administered intravenously in a dose of about 0.25–2.5 mg/kg/day for 2–5 days, a lower maintenance dosage is then continued, i.e., once or twice weekly, for as long as clinical improvement is evident. The dosage can be adjusted weekly according to the patient's tolerance.

The invention will be further described by reference to the following detailed examples.

EXAMPLE 1

Preparation and Characterization of the B43-Genistein (GEN) Immunoconjugate

The elution profile of the B43-GEN immunoconjugate was initially determined using an immunoconjugate prepared with $^{125}$I labeled GEN. $^{125}$I labeled GEN was also used to verify the removal of free GEN as well as GEN-labeled B43xB43 homoconjugates from the HPLC-purified 150 kDa B43-GEN immunoconjugate. The procedure used to carry out these studies is as follows.

Genistein (in 65% ethanol, 35% PBS, PH 7.5) was radioiodinated at room temperature in Reacti-Vials containing IODO-beads (Pierce Chemical Co., Rockford, Ill.) and $^{125}$I (Na, carrier-free, 17.4 Ci/mg, NEN, Boston, Mass.) as per manufacturer's instructions. After 15 minutes, the reaction mixture without the beads was removed from the vial and passed through an ULTRASEP disposable column containing 500 mg of silica (Phenomenex, Torrance, Calif.) to remove free iodide. $^{125}$I-labeled GEN was eluted from the silica column with a toluene:acetone:chloroform (40:35:25) mixture. Aliquots were counted in a gamma counter (Pharmacia LKB, Piscataway, N.J.) and subjected to thin layer chromatography on SILICA GEL G REDI-PLATES containing a fluorescent indicator (Fisher Scientific, Pittsburg, Pa.) to monitor the preparation. Purification of $^{125}$I-GEN was performed by scraping the desired material from a 20×20 cm TLC plate without indicator and eluting with DMSO. The specific activity of $^{125}$I-GEN was $2.6 \times 10^5$ cpm/nmol.

Purified B43 (5 mg/mL) was modified in a 2 hour reaction at room temperature via its primary amino groups using the succinimidyl-containing photoreactive (optimal photolysis at 265–400 nm) crosslinking agent Sulfo-SANPAH (40 mM solution in DMSO) (Pierce Chemical Co., Rockford, Ill.) at a 25:1 molar ratio of crosslinker to antibody. Excess crosslinker was removed by passing the reaction mixture through a PD-10 prepacked G25 column (Pharmacia LKB, Piscataway, N.J.). The modified B43 was then mixed with a 25:1 molar ratio of genistein (GEN; MW: 270.2) (Calbiochem, La Jolla, Calif.) (50 mM solution in DMSO) or $^{125}$I-labeled GEN and subsequently irradiated with gentle mixing for 10 min with UV light at wavelengths 254–366 nm using a multiband UV light emitter (Model UVGL-15 MINERALITE; UVP, San Gabriel, Calif.). Excess GEN or $^{125}$I-labeled GEN in the reaction mixture was removed by passage through a PD-10 column and 300 kDa B43-B43 homoconjugates with or without conjugated GEN. Higher molecular weight reaction products were removed by size exclusion HPLC.

The selective immunoreactivity of B43-GEN with B-lineage lymphoma cells was confirmed by measuring the immunoreactivity of B43-$^{125}$I-GEN with CD19 antigen positive RAMOS B-lineage lymphoma cells and CD19 antigen negative MOLT-3 T-lineage leukemia/lymphoma cells in the presence or absence of a 10-fold molar excess of cold B43 antibody using standard ligand binding assays. Uckun et al., *Blood*, 74, 761 (1989).

The purity of the B43-$^{125}$I-GEN immunoconjugate was assessed by SDS-PAGE (5% separating gels, nonreducing conditions) and autoradiography using intensifying screens and KODAK XAR-5 film. The final preparation was contaminated with <5% unconjugated B43 antibody or GEN and was found, in 4 independent conjugations, to contain on average one (range: 0.9–1.3) molecule of GEN per each B43 antibody molecule, as determined by the specific activity of immunoconjugates prepared using $^{125}$I-GEN.

EXAMPLE 2

Immune Complex Kinase Assays

Immune complex kinase assays were performed using acid-denatured rabbit enolase as an exogenous PTK substrate as previously described by Uckun et al. in *J. Biol. Chem.*, 268, 21172 (1993). The enzymatic activity of LYN kinase immunoprecipitated from NALM-6 cells was determined before and after a 4 hour incubation with B43-GEN or Sulfo-SANPAH modified B43 monoclonal antibody during a 10-min kinase reaction in the presence of [γ-$^{32}$P]ATP (50 μCi/μmol) as described by Uckun et al. in *J. Biol. Chem.*, 268, 21172 (1993). Control reagents included unmodified B43 monoclonal antibody, Sulfo-SANPAH modified B43 antibody, and TXU-GEN immunoconjugate which does not react with CD19$^+$ B-lineage lymphoma cells.

(mean±SE=4259±451) femtomols of B43-$^{125}$I-GEN were specifically bound to 10$^8$ target B-lineage leukemia cells. The estimated number of B43-$^{125}$I-GEN molecules bound per cell ranged from 2.1×10$^4$ to 3.1×10$^4$ (mean±SE= 2.6±0.3×10$^4$). By comparison, no binding was detected of B43-$^{125}$I-GEN to MOLT-3 T-lineage leukemia cells or HL60 acute myelocytic leukemia cells (Table 3).

We further examined by flow cytometry the binding of B43-GEN to CD19 antigen positive B-lineage leukemia cells using indirect immunofluorescence staining with a fluoresceinisothiocyanate (FITC) labeled goat-anti-mouse IgG as secondary antibody. B43-GEN stained NALM-6 cells with the same intensity as unconjugated B43 antibody over a broad range of concentrations; furthermore it competed as effectively as unconjugated B43 with phycoerythrin (PE) labeled B43 or Leu12 anti-CD19 antibodies for surface binding sites.

These results demonstrate that B43-GEN immunoconjugate selectively binds to CD19 antigen positive B-lineage leukemia cells.

EXAMPLE 3

Inhibition of CD19 Associated LCK kinase by B43-GEN

In order to determine whether LCK kinase was inhibited by B43-GEN when associated with CD19, RAMOS cells were treated with nanomolar concentrations of the immunoconjugate for 4 hours at 37° C., with the indicated concentrations of B43-GEN, pelleted, and lysed in Nonidet P-40 lysis buffer. Immune complex kinase assays were performed using acid-denatured rabbit enolase as an exogenous PTK substrate as previously described by Uckun et al. in *J. Biol. Chem.*, 268, 21172 (1993). Controls were treated with TXU(anti-CD7)-GEN immunoconjugate directed against the CD7/Tp41 T-cell surface antigen, unconjugated and unmodified B43 antibody, or SANPAH-modified unconjugated B43 antibody.

As is shown by FIG. 1A, B43-GEN treatment of RAMOS cells at nanomolar concentrations results in inhibition of LCK kinase, as reflected by decreased autophosphorylation or decreased enolase substrate phosphorylation. This inhibition was associated with a marked decrease of phosphorylation on tyrosine residues of abundant protein substrates

TABLE 3

Selective Binding of B43 (anti-CD 19)-GEN Immunoconjugate to CD19$^+$ Leukemic Cells

| | | B43 (anti-CD19)-[$^{125}$I]-GEN Binding | | | | |
|---|---|---|---|---|---|---|
| | | % Inhibitable Binding | | | | |
| Cell Line | Immunophenotype | Excess α-CD19 | Excess α-CD7 | Specific Binding (cpm/10$^8$ cells) | Fentomoles/ 10$^8$ cells | Molecules/ cell × 10$^4$ |
| NALM-6 | CD19$^+$ pre-B ALL | 33.6 | 0 | 900 (±28) | 5000 (±155) | 3.1 (±0.1) |
| NALM-16 | CD19$^+$ pro-B ALL | 34.2 | 0 | 780 (±32) | 4333 (±178) | 2.7 (±0.1) |
| RAMOS | CD19$^+$ B-ALL | 28.6 | 0 | 620 (±20) | 3444 (±111) | 2.1 (±0.1) |
| MOLT-3 | CD19$^-$ T-ALL | <0.1 | ND | <10 | NE | NE |
| HL60 | CD19$^-$ AML | <0.1 | ND | <10 | NE | NE |

As shown in Table 3, B43 antibody blocked the binding of B43-$^{125}$I-GEN to CD19 positive target NALM-6, NALM-16, and RAMOS cells by 32.1±1.8%, whereas no blocking was observed with ten-fold molar excess of the irrelevant control antibody TXU (anti-CD7). 3444–5000 in RAMOS cells, as determined by immunoblotting with a polyclonal antiphosphotyrosine antibody (FIG. 1B). Unlike B43-GEN, neither unconjugated B43 antibody nor the control immunoconjugate TXU(anti-CD7)-GEN inhibited LCK kinase (FIG. 1A) or decreased tyrosine phosphorylation (FIG. 1B). These results indicate that both the tyrosine kinase inhibitory activity of GEN as well as the CD19 targeting ability of the B43 monoclonal antibody are required for B43-GEN induced inhibition of LCK kinase in Burkitt's lymphoma cells.

EXAMPLE 4

Inhibition of CD19-Associated LYN Kinase by B43-GEN

In order to determine whether LYN kinase was inhibited by B43-GEN when associated with CD19, NALM-6 cells were treated with nanomolar concentrations of the immunoconjugate for 4 hours, and the protein tyrosine kinase activity of LYN was estimated by immune complex protein kinase assays. Controls were treated with unconjugated GEN, TXU(anti-CD7)-GEN immunoconjugate directed against the CD7/Tp41 T-cell surface antigen, unconjugated and unmodified B43 antibody, or SANPAH-modified unconjugated B43 antibody.

Figure 1C:
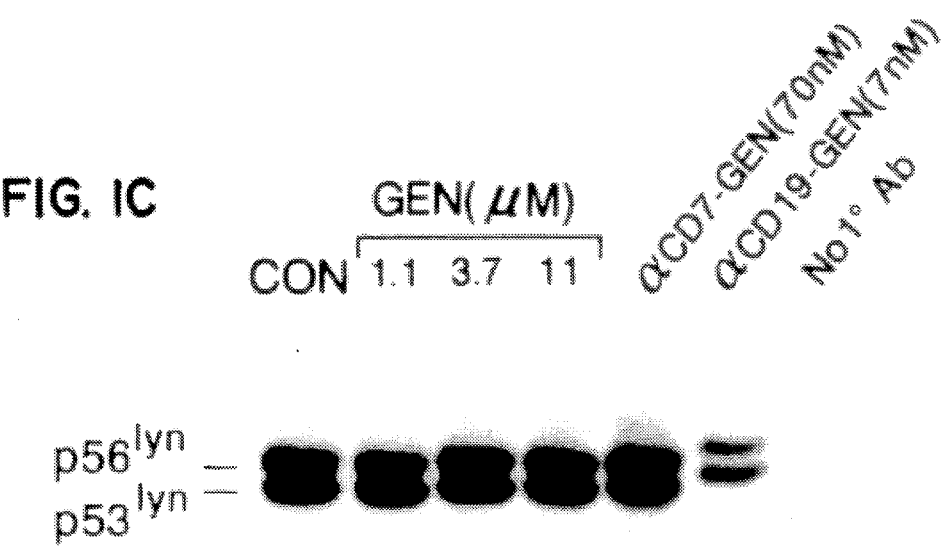
Figure 1D:
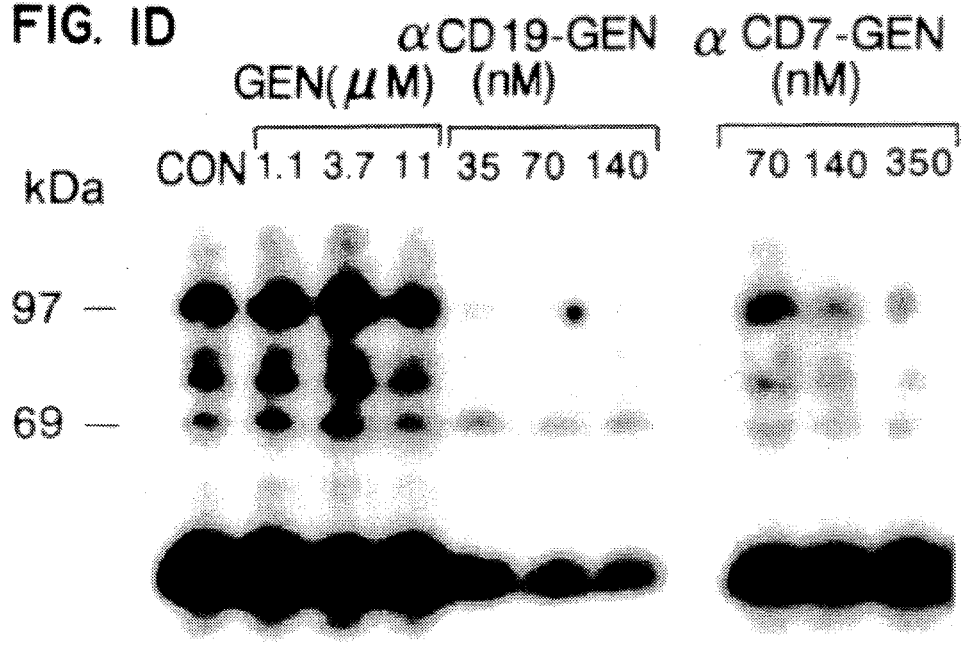
Figure 1E:
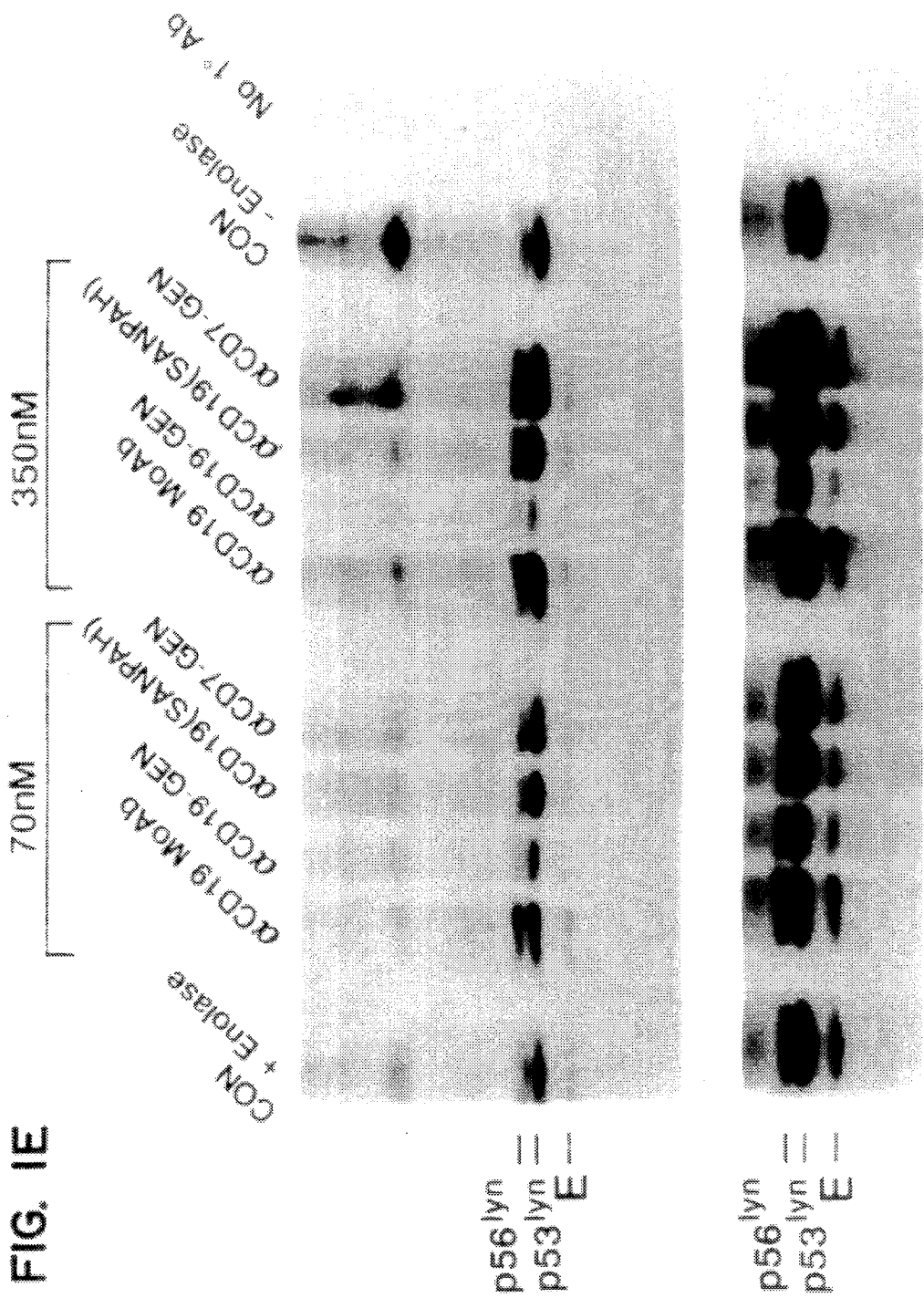

B43-GEN treatment at nanomolar concentrations resulted in inhibition of LYN kinase, as reflected by decreased autophosphorylation or enolase substrate phosphorylation (FIG. 1C & E). The abundance of the enzyme, as determined by anti-LYN immunoblotting, did not change during the course of the experiment, which is consistent with decreased specific activity. Inhibition of LYN kinase after B43-GEN treatment was associated with marked tyrosine dephosphorylation of abundant protein substrates in NALM-6 cells, as determined by immunoblotting with a polyclonal antiphosphotyrosine antibody (FIG. 1D). By comparison, micromolar concentrations of unconjugated GEN failed to affect the enzymatic activity of LYN (FIG. 1C) or the baseline phosphorylation status of tyrosine phosphorylated proteins (FIG. 1D).

The results of these experiments reveal that B43-GEN immunoconjugate is >1571-times more effective than unconjugated GEN at inhibiting LYN kinase and causing tyrosine dephosphorylation in NALM-6 cells. Unlike B43-GEN, neither unconjugated B43 antibody (derivatized or underivatized) nor the control immunoconjugate TXU-GEN inhibited LYN kinase (FIGS. 1C,D,E,), indicating that both the tyrosine kinase inhibitory GEN moiety as well as the CD19-specific B43 monoclonal antibody moiety are required for the B43-GEN induced inhibition of LYN kinase in B-lineage leukemia cells.

Figure 1F:
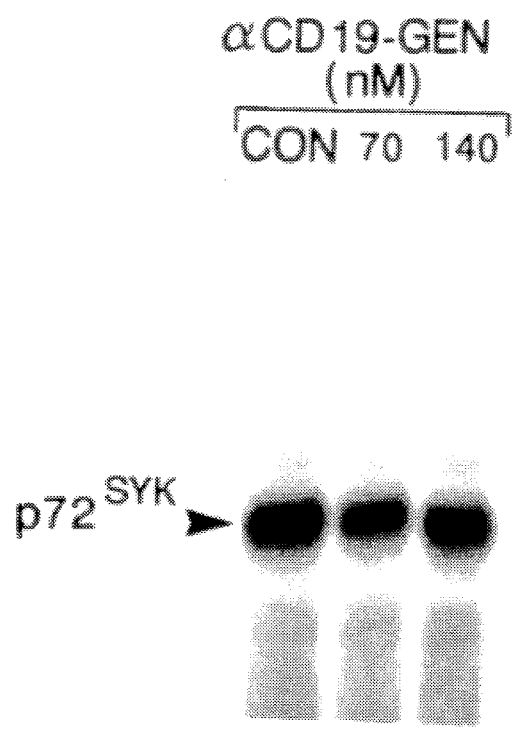
Figure 1G:
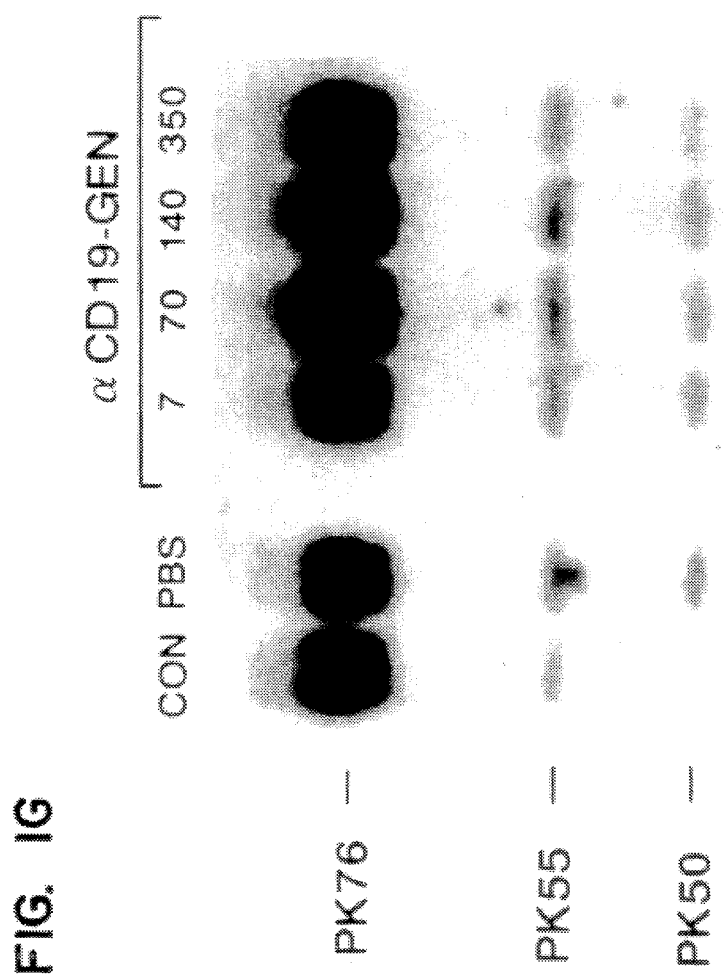

In other experiments, it has been shown that B43-GEN effectively inhibits LYN Kinase in K562 erythroleukemia cells transfected with human CD19 cDNA but the immunoconjugate does not inhibit LYN kinase in untransfected K562 erythroleukemic cells or stable K562 transfectants expressing the CD19 deletion mutant A308, which is truncated on exon 6 and has no tyrosine residues that allow association with the SH2 domain of the LYN kinase. Thus, B43-GEN inhibits LYN kinase only if this kinase is associated with the CD19 receptor. SYK kinase, which is not associated with the CD19 receptor, was not inhibited after treatment of NALM-6 cells with B43-GEN (FIG. 1F), whereas LCK, another Src family PTK abundantly expressed in RAMOS cells in association with the CD19 receptor showed marked inhibition. These results demonstrate that B43-GEN inhibits only those PTK in B-lineage leukemia cells which are associated with the CD19 receptor. The effects of B43-GEN treatment on the enzymatic activity of PKC and PKC dependent renaturable serine kinases in CD19+ leukemia cells was also examined. As evidenced in FIG. 1G, serine kinases were not inhibited by B43-GEN even at a concentration of 350 nM.

Using the same protocol as described above, the abilities of B43-quercetin, B43-daidzein and B43-amino-genistein to inhibit the activity of Lyn kinase were also evaluated. Briefly, daidzein or quercetin were linked to B43 with the crosslinker sulfo-SANPAH and NALM-6 pre-B leukemia cells were treated with the resulting immunoconjugate. SPDP was used to prepare B43-amino-genistein. Results of these experiments showed that B43-quercetin, B43-daidzein and B43-amino-genistein inhibited the activity of Lyn kinase in a dose dependent fashion and furthermore, resulted in rapid apoptotic death of the leukemia cells. However, they were less effective than B43-GEN.

Taken together, these experiments demonstrate that the B43(anti-CD19)-GEN immunoconjugate is a potent and cell-type specific PTK inhibitor which selectively inhibits CD19-associated PTK in B-lineage leukemia cells.

EXAMPLE 5

Effect of B43-GEN on Topoisomerase II Enzyme

Figure 2:
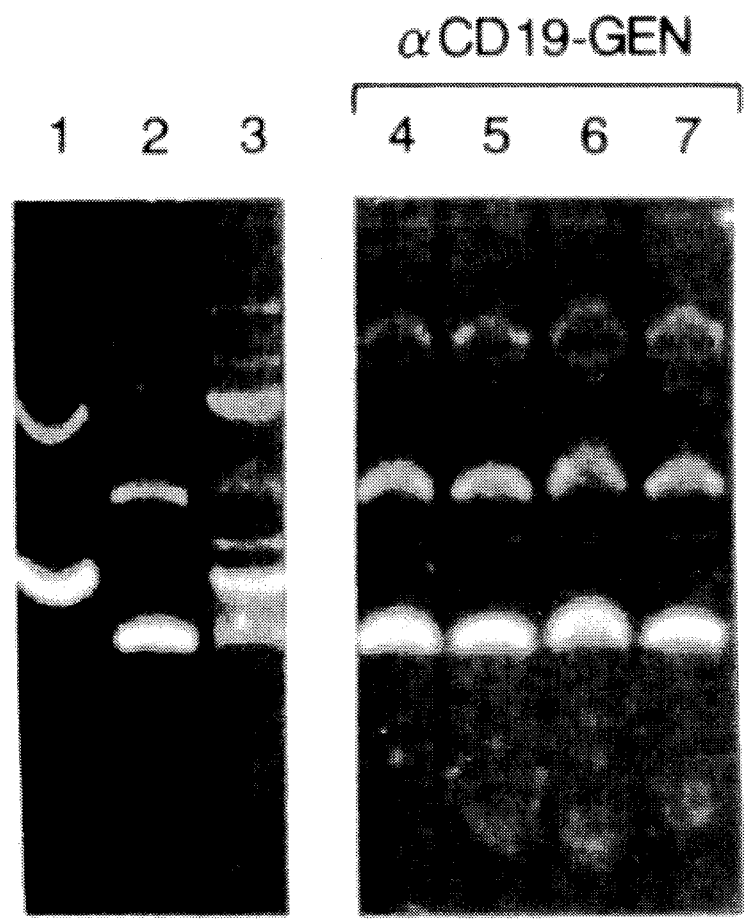
FIG. 2 depicts a gel which demonstrates that topoisomerase II enzyme is not inhibited by B43-GEN.

A Topoisomerase II Drug Screening kit (Topogen, Inc., Columbus, Ohio) was used to examine the effects of B43-GEN on topoisomerase II enzyme. The kit is based upon formation of DNA cleavage products after treatment of a supercoiled DNA substrate (pRYG) containing a single high affinity topoisomerase II recognition and cleavage site. As shown in FIG. 2, lane 2, pRYG is converted to relaxed monomers and dimers following incubation with human topoisomerase II enzyme. FIG. 2, Lane 3 further shows that the topoisomerase II inhibitor teniposide (VM-26) impairs the ability of human topoisomerase II to relax the supercoiled DNA substrate. By comparison, topoisomerase II enzyme was not inhibited even at micromolar concentrations of B43-GEN (FIG. 2, Lanes 4–7).

EXAMPLE 6

Apoptosis Assays

After various incubation times with the B43-GEN immunoconjugate, RAMOS cells were analyzed for apoptotic changes by DNA flow cytometry as described by Darrynkiewicz et al. in *Cytometry*, 13, 795, (1992). In addition, cells were harvested from 30 minutes to 24 hours after exposure to the B43-GEN immunoconjugate and DNA was prepared for analysis of fragmentation. DNA was then electrophoresed through a 1% agarose gel and visualized by UV light after staining with ethidium bromide.

Figure 2A:
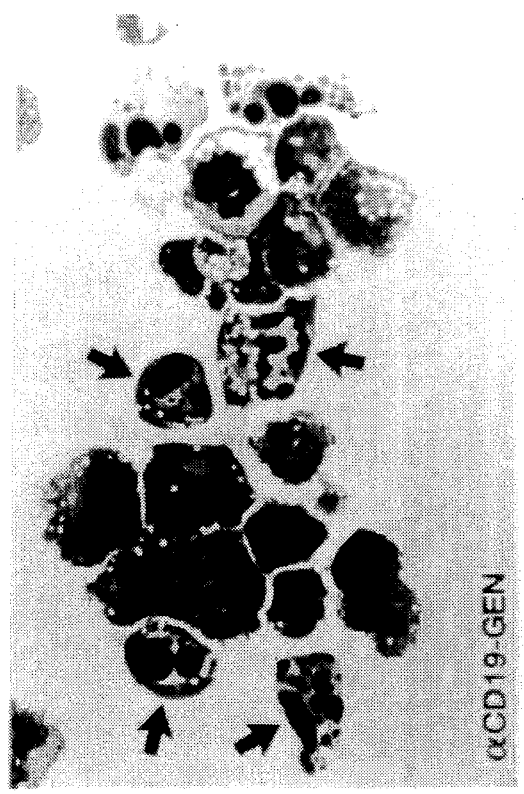
Figure 2A:
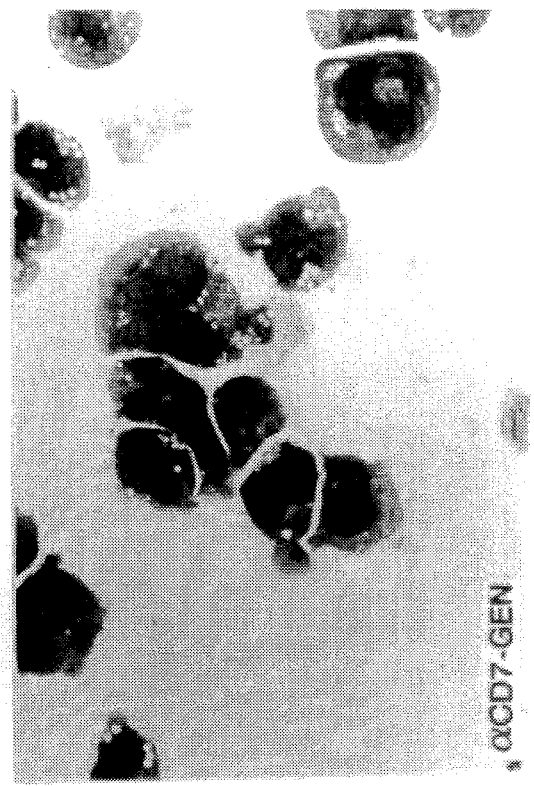
Figure 2A:
Figure 2A:
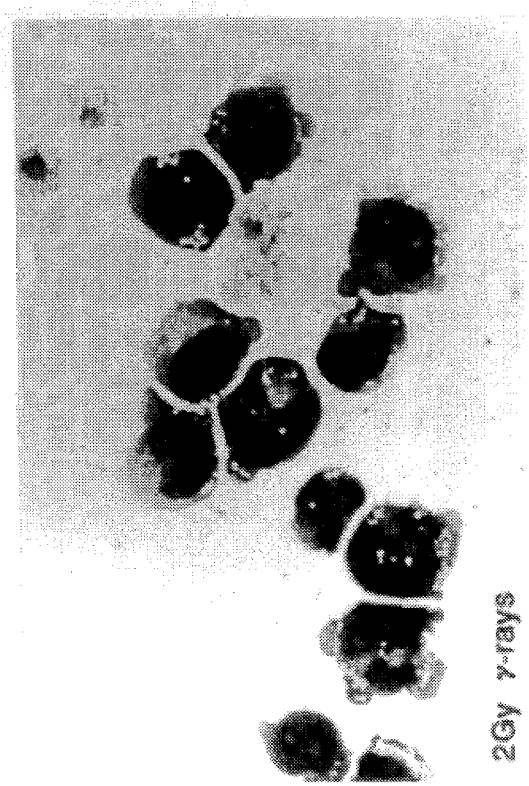
Figure 3:
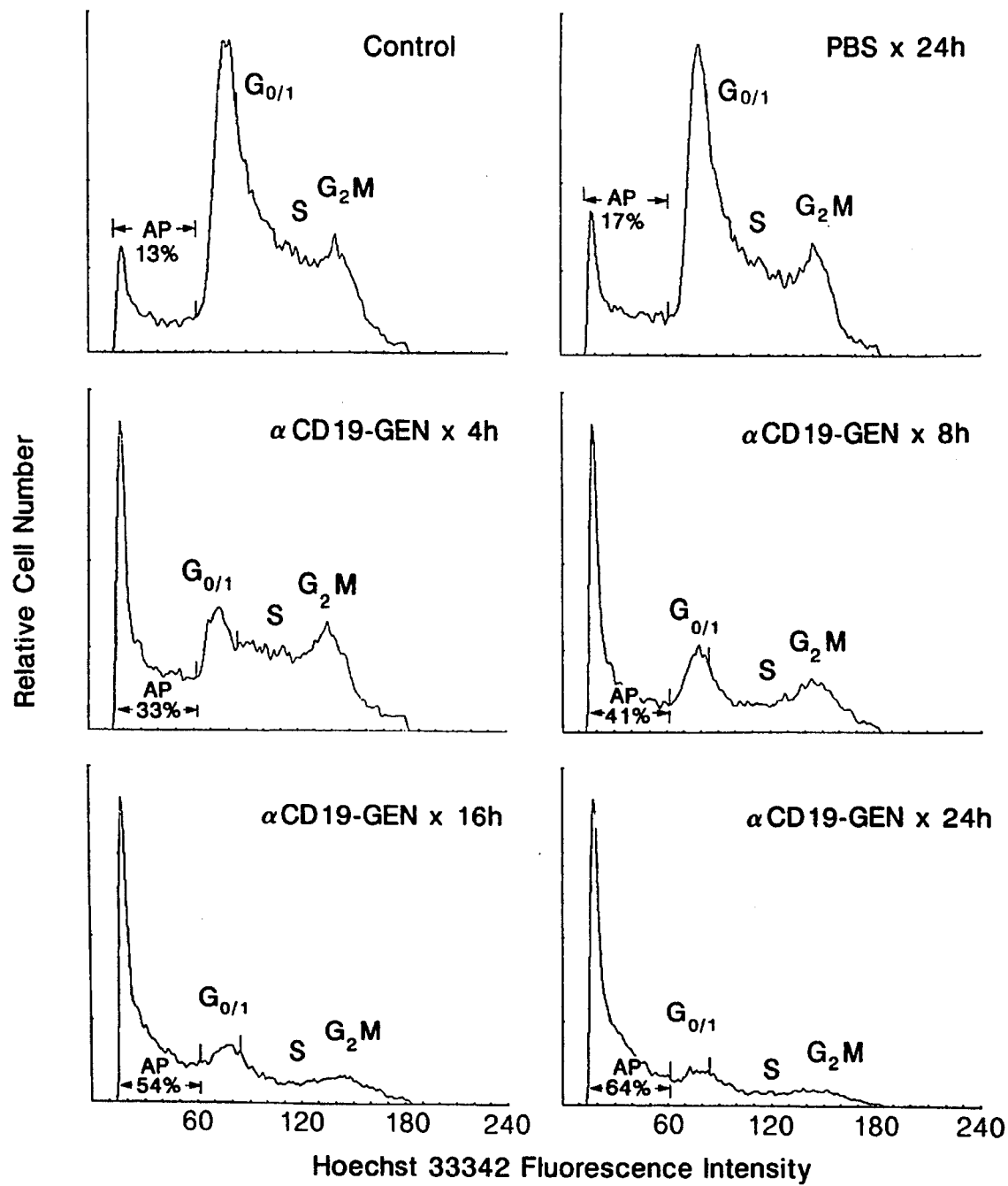
FIG. 3 is a depiction of DNA flow cytometric analyses of B43-GEN treated RAMOS lymphoma cells which demonstrates that 64% of cells become apoptotic within 24 hours of treatment.

B43-GEN induced apoptosis of RAMOS cells within 4 hours and of NALM-6 cells within 8 hours as evidenced by distinctive morphologic changes visualized by light microscopy. Indications of extensive cellular damage included shrinkage, nuclear chromatin condensation, segmentation of the nucleus, and plasma membrane blebs in >75% of cells (FIG. 2A). At 24 hours after initiation of B43-GEN treatment, 64% of RAMOS cells were apoptotic as seen by DNA flow cytometry (FIG. 3). B43-GEN (70 nM) was clearly more effective at destroying target leukemia cells than 2 Gy γ-rays.

Figure 4A:
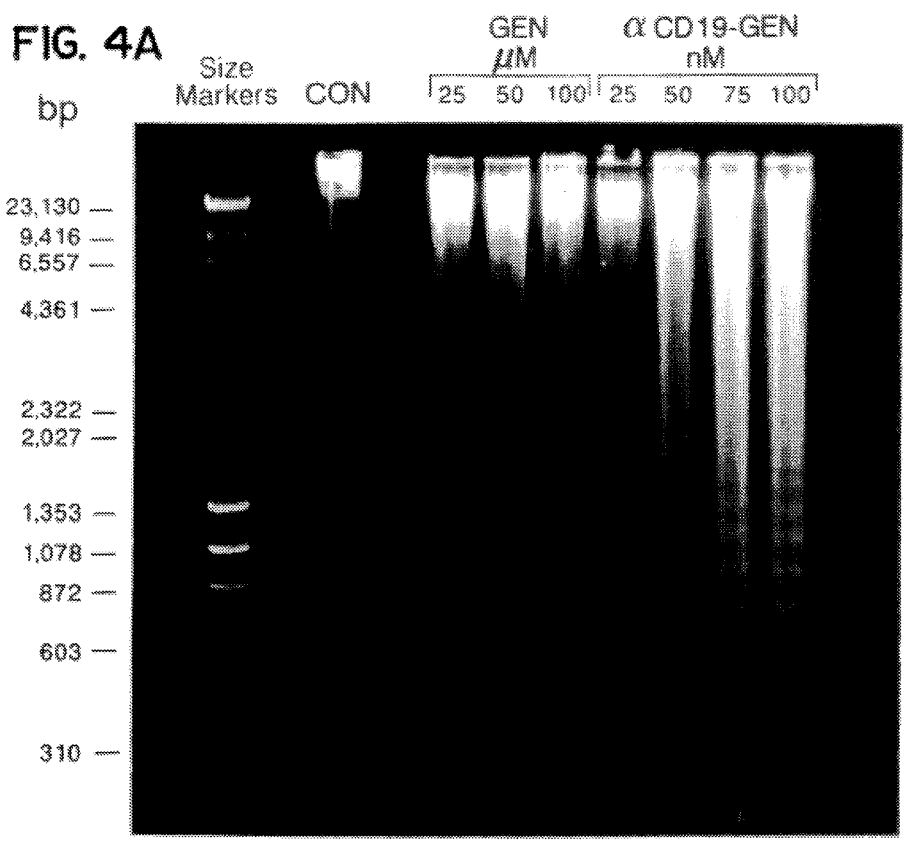
FIGS. 4A and B depict the DNA fragmentation in B43-GEN treated RAMOS lymphoma cells.
Figure 4A:
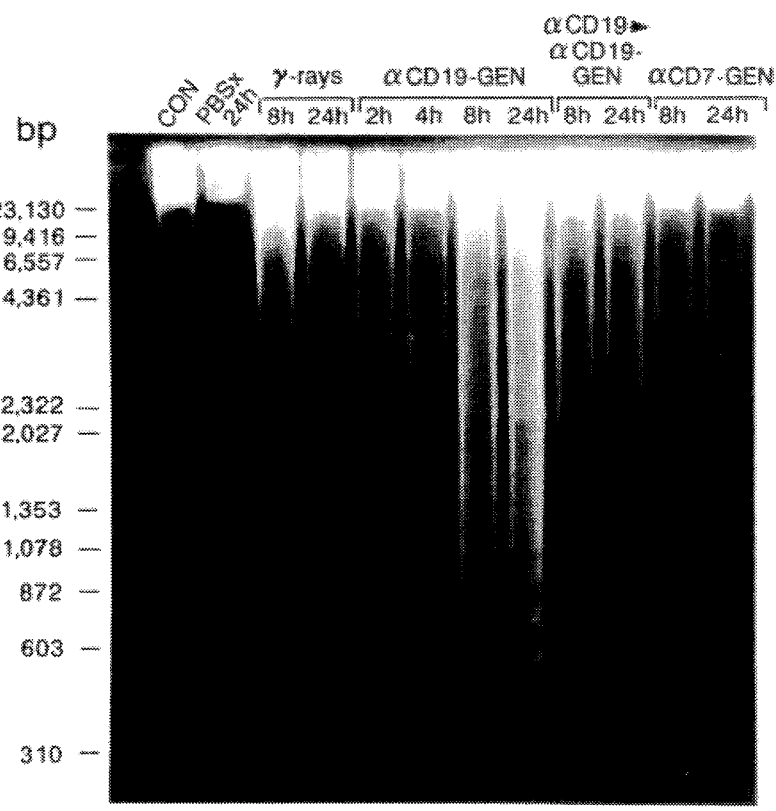
Figure 4B:
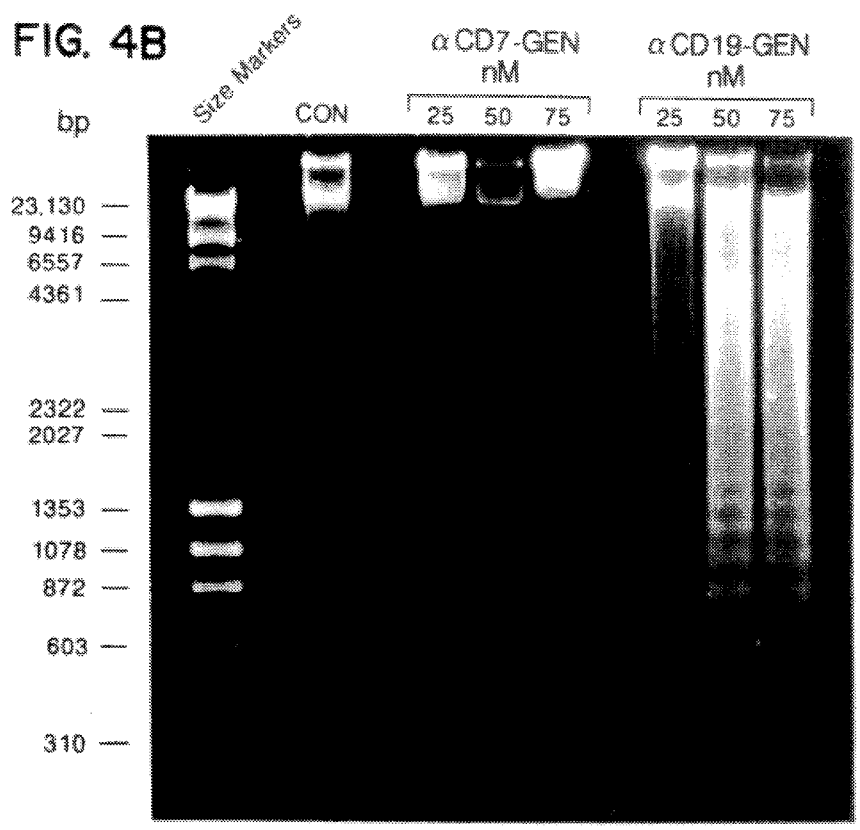
Figure 4B:
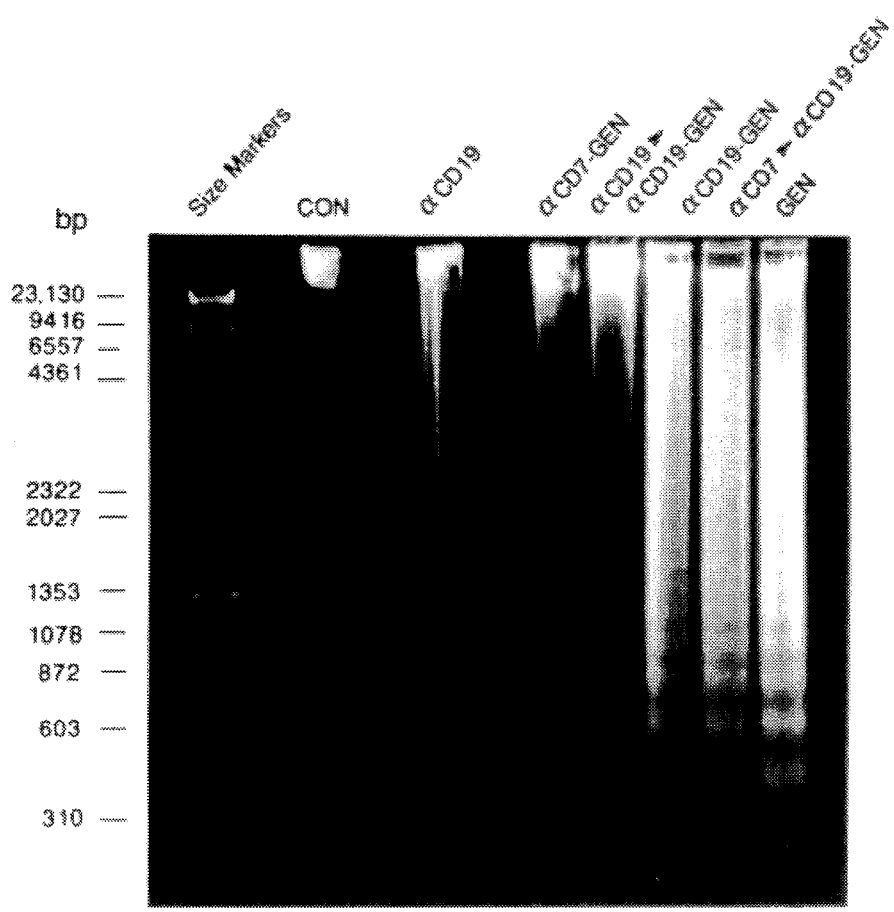

Agarose gel electrophoresis of DNA from B43-GEN treated B-lineage leukemia cells further confirmed the ability of the immunoconjugate to induce apoptosis. RAMOS cells treated with nanomolar concentrations of B43-GEN for 8–24 hours showed a ladder-like fragmentation pattern consistent with an endonucleolytic cleavage of DNA into oligonucleosome-length fragments at multiples of 200 base pairs, whereas DNA from cells treated with micromolar concentrations of unconjugated GEN showed no fragmentation (FIG. 4A & B). Remarkably, B43-GEN was able to induce apoptosis in highly radiation resistant RS4;11 leukemia cells (FIG. 4A, lower panel). B43-GEN induced apoptosis was CD19-receptor specific since (a) control immunoconjugate TXU-GEN directed against the CD7/Tp41 T-cell antigen did not induce apoptosis (FIG. 4A, lower panel and FIG. 4B), and (b) cell death could be prevented by preincubation of CD19 positive leukemia cells with 10-fold molar excess of unconjugated B43 antibody but not with 10-fold molar excess of TXU(anti-CD7) antibody (FIG. 4A & B, lower panels). Apoptosis of leukemia cells was triggered by the GEN moiety of the immunoconjugate since high concentrations of unconjugated GEN but not unconjugated B43 antibody induced DNA fragmentation (FIG. 4B, lower panel).

Taken together, the results of these experiments establish that B43-GEN immunoconjugate is an active anti-B-lineage leukemia agent in vitro.

EXAMPLE 7

Uptake of B43(Anti-CD19)-GEN by Target Leukemia Cells In Vitro

Figure 5:
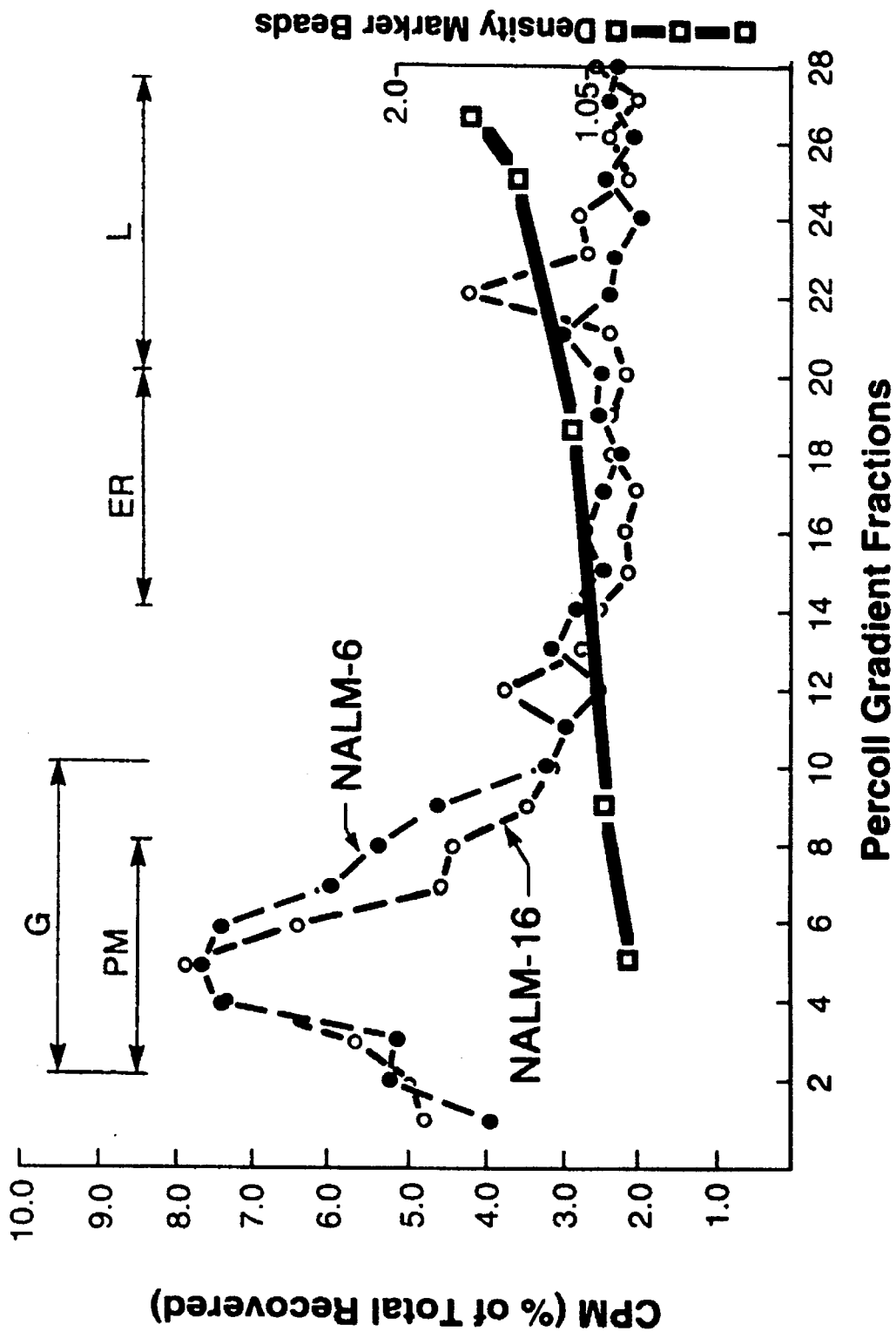
FIG. 5 is a graph depicting of the fate of cell-bound B43-GEN immunoconjugate. Density marker beads were used to determine gradient density. The indicated gradient regions for plasma membranes (PM), Golgi (G), endoplasmic reticulum (ER), and lysosomes (L) were determined based upon the characteristic distribution profile of the marker enzymes 5'-nucleotidase, galactosyltransferase, neutral α-glucosidase, and hexosamidinase, respectively. Dickson et al. *Biochemistry*, 22, 5667 (1983).

The destination of surface bound B43-$^{125}$I-GEN was traced in CD19 positive B-lineage leukemia cell lines NALM-6 and NALM-16. Leukemia cells were homogenized after 18 hours of treatment with the immunoconjugate, and various subcellular components were fractionated on Percoll density gradients. A significant portion of B43-$^{125}$I-GEN, representing 39% of the total cpm recovered from the in situ generated Percoll gradient, was localized in the plasma membrane or Golgi compartments of NALM-6 cells, as confirmed by cosedimentation with 5'-nucleotidase (a marker for plasma membrane) and galactosyltransferase (a marker for Golgi). Dickson et al., *Biochemistry*, 22, 5667 (1983). The remainder of radioactivity representing internalized B43-$^{125}$I-GEN was associated with soluble cytoplasmic fraction (15% of total cpm; Percoll gradient fractions 1–3; density <1.043 g/mL), endoplasmic reticulum (26% of total cpm; Percoll gradient fractions 10–19; density range: 1.049–1.056 g/mL), and lysosomes (14% of total cpm; Percoll gradient fractions 20–25; density range: 1.056–1.069 g/mL). Similar results were obtained with NALM-16 cells (FIG. 5).

The results of these experiments demonstrate that within 18 hours after binding to the CD19 receptor, more than half of the B43-GEN molecules are internalized, while the remaining minority continue their association with the membrane/Golgi fraction.

EXAMPLE 8

Anti-Tumor Activity of B43-GEN in a SCID Mouse Model of Human B-lineage Lymphoma SCID mice challenged with 5×10$^6$ RAMOS cells received three consecutive daily i.p. injections of B43-GEN (total=25 μg/mouse=168 pmols/mouse, 10-fold<the maximum tolerated dose) starting 24 hours after lymphoma cell inoculation. Control mice were treated with unconjugated GEN (10 μg/mouse=37 nmols/mouse), unconjugated B43 monoclonal antibody (50 μg/mouse=335 pmols/mouse), TXU(anti-CD7)-GEN control immunoconjugate (50 μg/mouse=335 pmols/mouse), or PBS. For comparison, some mice were treated with B43-pokeweed antiviral protein (PAP) immunotoxin (total=25 μg/mouse), which is an active anti-leukemia agent. Uckun et al., *J. Exp. Med.*, 163, 347 (1986). Survival of the mice was monitored by daily observation and event times were measured from the day of inoculation of lymphoma cells to the day of death. The probability of event-free survival was determined and event-free interval curves were generated using the Kaplan-Meier product limit method as described by Uckun et al. *New Engl. J. Med.*, 329, 1296 (1993).

Figure 6A:
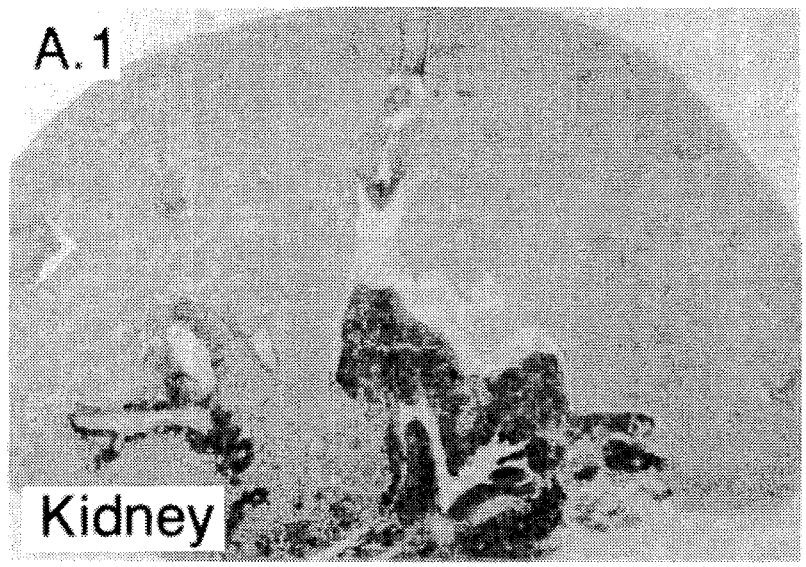
FIG. 6[A] is a depiction of the forensic disposition of SCID mice inoculated with RAMOS cells. Kidney (A.1 and A.2): A dense pelvic infiltrate as well as several perivascular cortical infiltrates of highly pleomorphic lymphoid cells were apparent. Liver (B.1 and B.2): Generalized infiltration of portal areas by pleomorphic lymphoid cells with a high mitotic rate was observed. Stomach (C.1 and C.2): A mass of highly pleomorphic lymphoid cells was attached to the serosal surface. Lymphoma cells invaded the wall of the organ and distended the submucosal region.
Figure 6A:
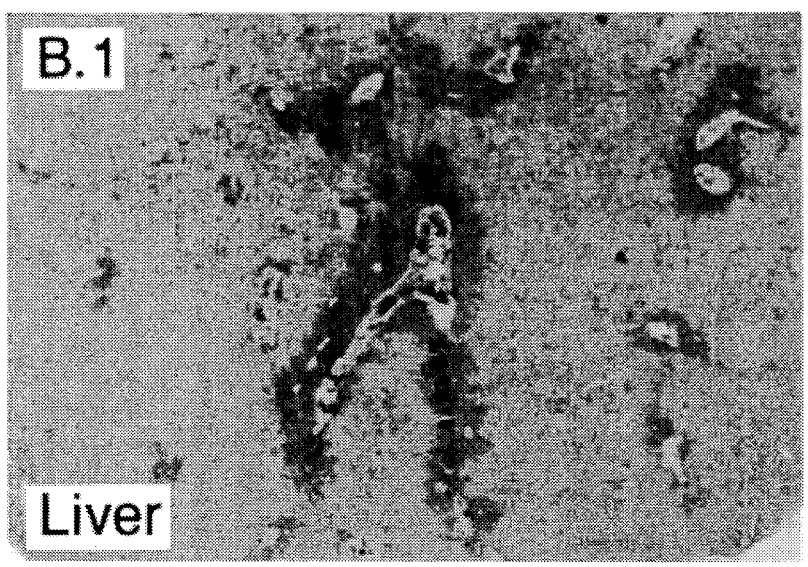
Figure 6A:
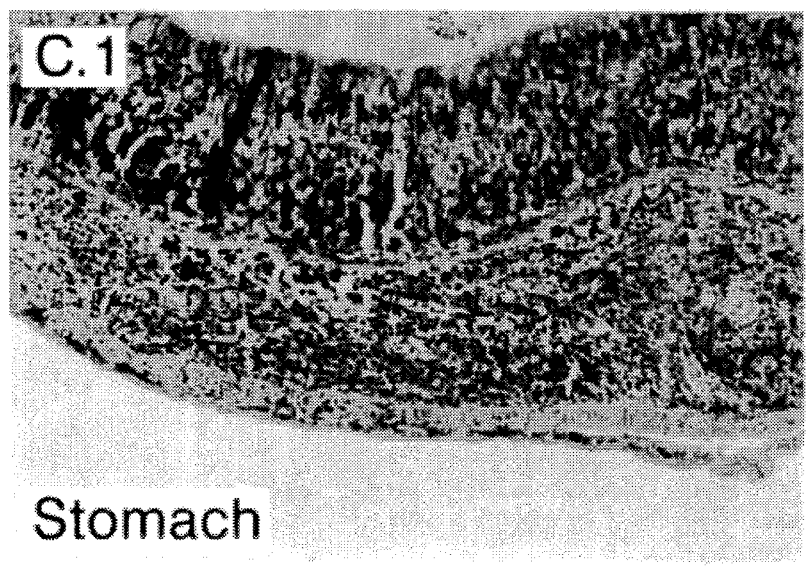
Figure 6A:
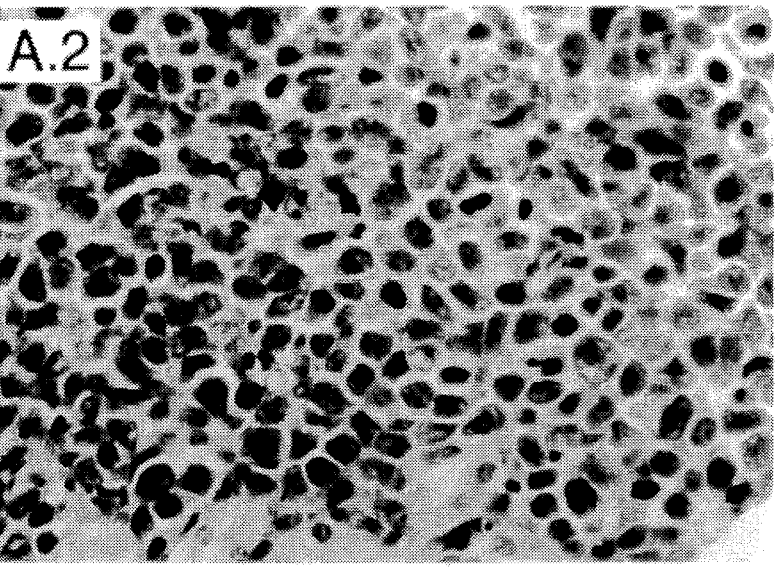
Figure 6A:
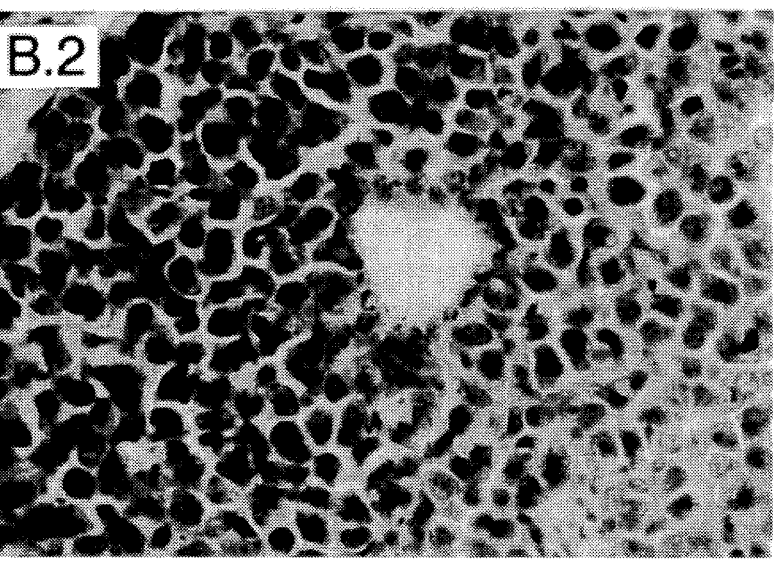
Figure 6A:
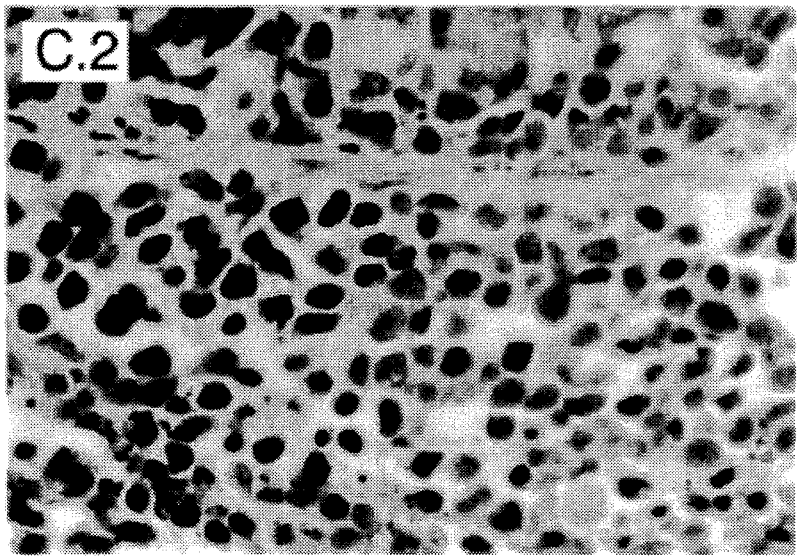

All control mice treated with PBS, unconjugated GEN (10 μg/mouse=37 nmols/mouse), unconjugated B43 antibody (50 μg/mouse=335 pmols/mouse), TXU(anti-CD7)-GEN control immunoconjugate (50 μg/mouse=335 pmols/mouse), or B43-PAP immunotoxin (25 μg/mouse) died of disseminated human Burkitt's lymphoma at 24 to 61 days after inoculation (median event-free survival=48.0 days) (FIG. 6A and B). These mice had large abdominal masses with extensions to the abdominal organs. Sheets of neoplastic cells obliterated the normal tissue elements of bone marrow, spleen, and abdominal nodes. Colonization of the brain was apparent by the presence of thin rafts of lymphoma cells in the leptomeninges and in some cases, extensive invasion by lymphoma cells was seen in gray matter of the cerebral cortex and brain stem. The heart showed thin, short rafts in the epicardium, and the alveolar septa of the lung contained a light infiltrate of RAMOS cells. Kidneys (FIGS. 6.A.1 & 6.A.2) had large accumulations in perirenal fat, as well as light to extensive interstitial accumulations and small numbers of neoplastic perivascular cuffs in the cortex. Large accumulations were visible in the portal areas of the liver (FIGS. 6.B.1 & 6.B.2), along with numerous small nests in the sinusoidal and subcapsular spaces. The mitotic rate was very high, averaging 15–20 mitotic figures per high-power field in most tissues and up to 40–50 per high-power field in some areas.

Figure 6B:
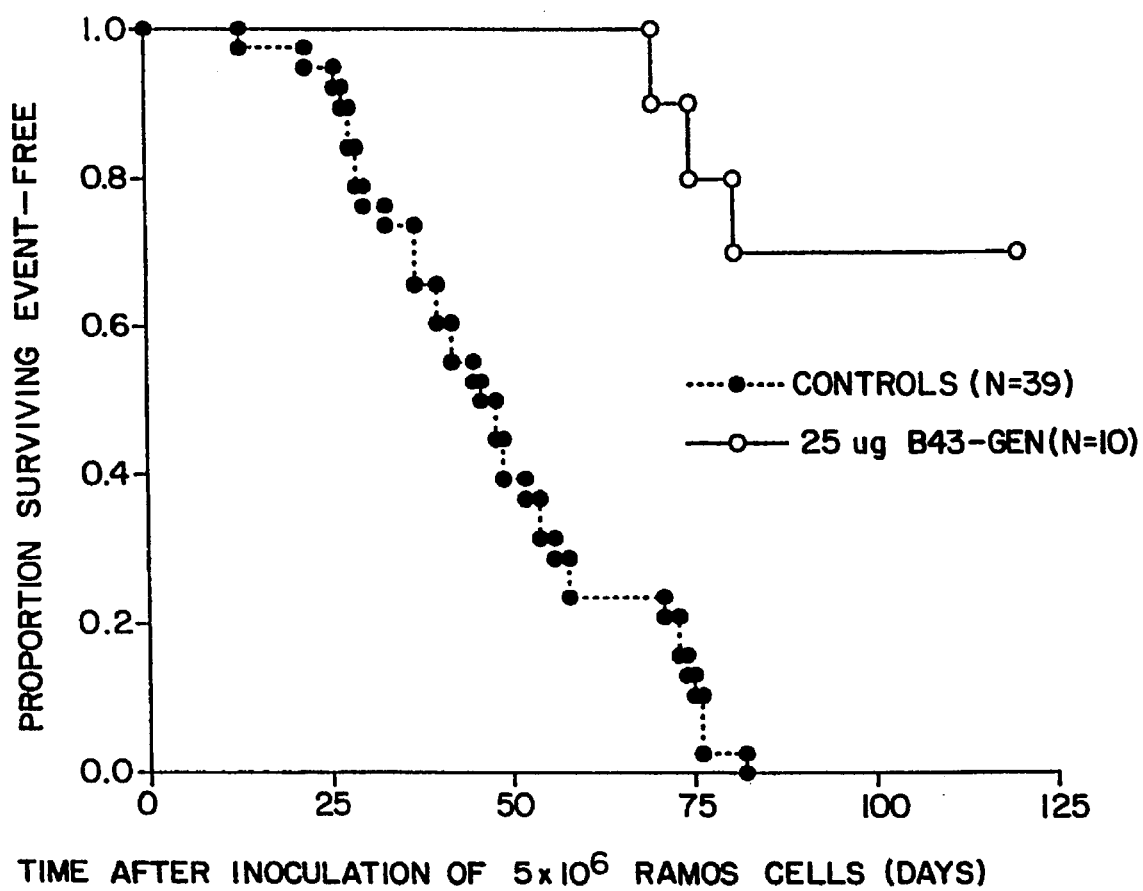

In contrast, B43-GEN prevented disseminated human Burkitt's lymphoma in the majority of SCID mice. Seven of 10 mice treated with the B43-GEN immunoconjugate (25 μg/mouse=168 pmols/mouse, ten-fold lower than the maximum tolerated dose) remained alive without clinical evidence of lymphoma for >4 months (probability of event-free survival at 100 days=70±15%; median event-free survival >125 days) (FIG. 6B).

EXAMPLE 9

Figure 7A:
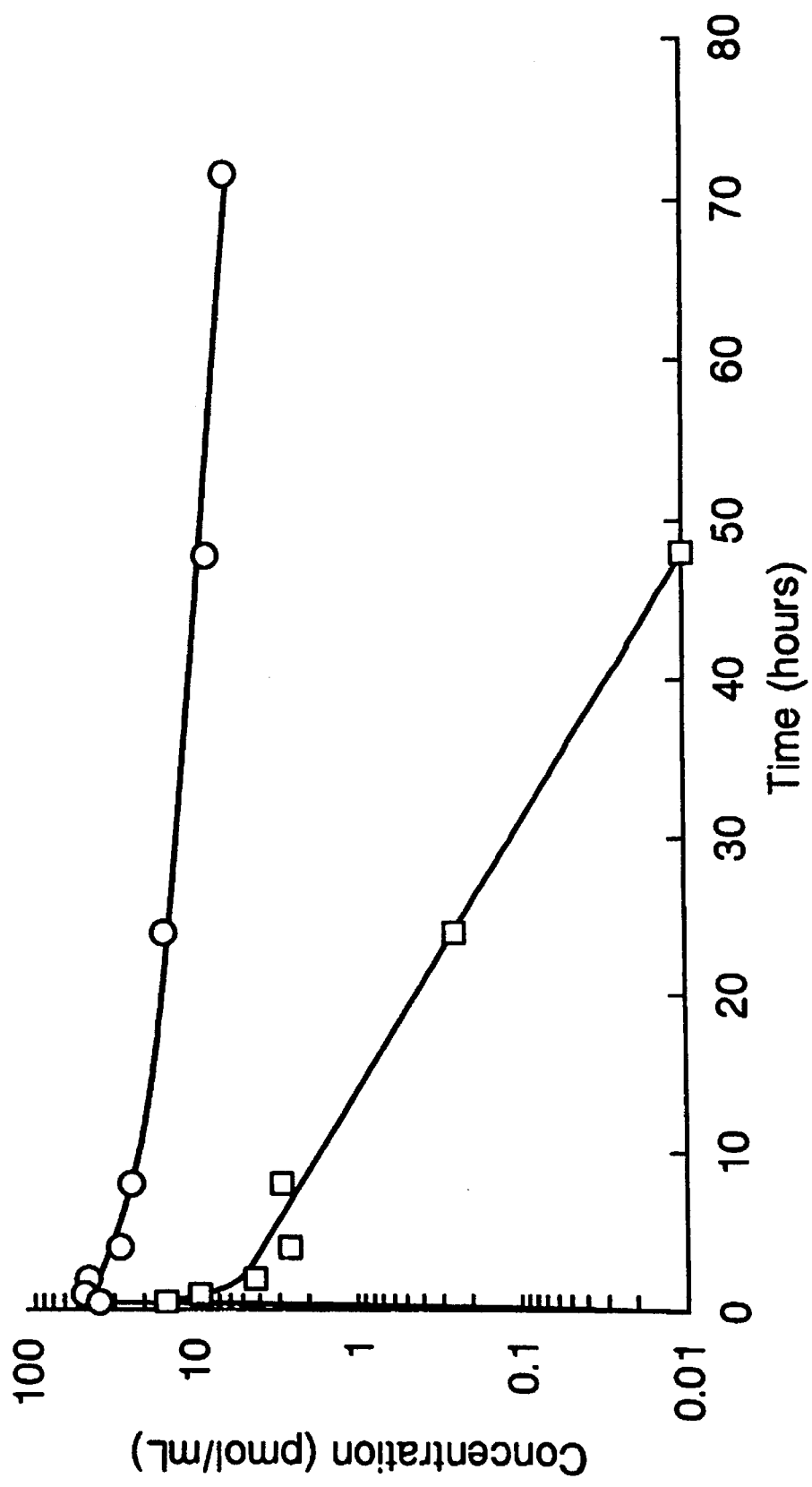
FIG. 7[A] is a depiction of the plasma concentrations vs time curves for B43-GEN immunoconjugate (-□-) and unconjugated GEN (-o-), following injection of 58 pmol into SCID mice challenged with $1 \times 10^6$ NALM-6 leukemia cells 24 hours earlier. Lines represent two-compartment model simulations, symbols depict measured concentrations.

Pharmacokinetic Features and Anti-Leukemic Activity of B43-GEN in a SCID Mouse Model of Human B-lineage Leukemia The pharmacokinetic features of B43-GEN was evaluated in a SCID mouse model with human B-lineage leukemia as follows. SCID mice challenged with NALM-6 cells were treated with either 25 μg/mouse=168 pmols/mouse (>10-fold lower than the MTD) or 50 μg/mouse=335 pmols/mouse (>5-fold lower than the MTD). All control mice were treated with unconjugated GEN (10 μg/mouse=37 nmols/mouse), unconjugated B43 antibody (50 μg/mouse=335 pmols/mouse), TXU(anti-CD7)-GEN control immunoconjugate (50 μg/mouse=335 pmols/mouse), or PBS. As shown in FIG. 7A and Table 4, B43-GEN immunoconjugate has a significantly longer elimination half-life and slower plasma clearance than unconjugated GEN.

TABLE 4

Two Compartment Pharmacokinetic Model Parameters for Tyrosine Kinase Inhibitors in SCID Mice

| | B43 (anti-CD19-GEN) | | GEN |
|---|---|---|---|
| | Minimal Leukemia Burden | End Stage Leukemia | Minimal Leukemia Burden |
| Dose [pmol] | 57.7 | 71.1 | 58.3 |
| Vc [μL/g] | 52.0 | 63.9 | 87.0 |
| Ke [1/h] | 0.037 | 0.052 | 0.574 |
| Kcp [1/h] | 0.078 | 0.069 | 1.341 |
| Kpc [1/h] | 0.096 | 0.163 | 0.549 |
| $T_{½β}$ [h] | 37.5 | 20.5 | 5.1 |
| Cl [μL/h/g] | 1.9 | 3.3 | 49.7 |

Vc = central volume of distribution; Ke = elimination rate constant; Kcp = distribution rate constant from central to peripheral compartment; Kpc = distribution rate constant from peripheral to central compartment; $T_{½β}$ = elimination half-life; Cl = sytemic clearance from plasma.

TABLE 5

Tissue Distribution Parameters for Tyrosine Kinase Inhibitors in SCID Mice

| | Linear Binding Constant (R) | | |
|---|---|---|---|
| | B43 (Anti-CD19-GEN) | | GEN |
| Tissue | Minimal Leukemia Burden | End Stage Leukemia | Minimal Leukemia Burden |
| Lungs | 0.221 | 0.339 | 0.531 |
| Brain | 0.008 | 0.012 | 0.027 |
| Heart | 0.117 | 0.236 | 0.335 |
| Skin | 0.061 | 0.10 | 0.208 |
| Spleen | 0.145 | 0.323 | 0.040 |
| Kidney | 0.118 | 0.162 | 0.253 |
| Muscle | 0.016 | 0.028 | 0.095 |
| Femur | 0.031 | 0.109 | 0.00008 |
| Liver | 0.139 | 0.290 | 0.50 |
| Rest of Body* | 0.033 | 0.055 | 1.11 |
| Clearance, μL/h/g | | | |
| Kidney | 0.56 | 1.4 | 18.7 |
| Liver | 1.2 | 1.2 | 40.9 |
| Total Clearance | 1.76 | 2.6 | 59.6 |

R = Tissue to plasma equilibrium distribution ratio for linear binding.
*= Residual amount of drug not accounted for by tissues studied.

Figure 7B:
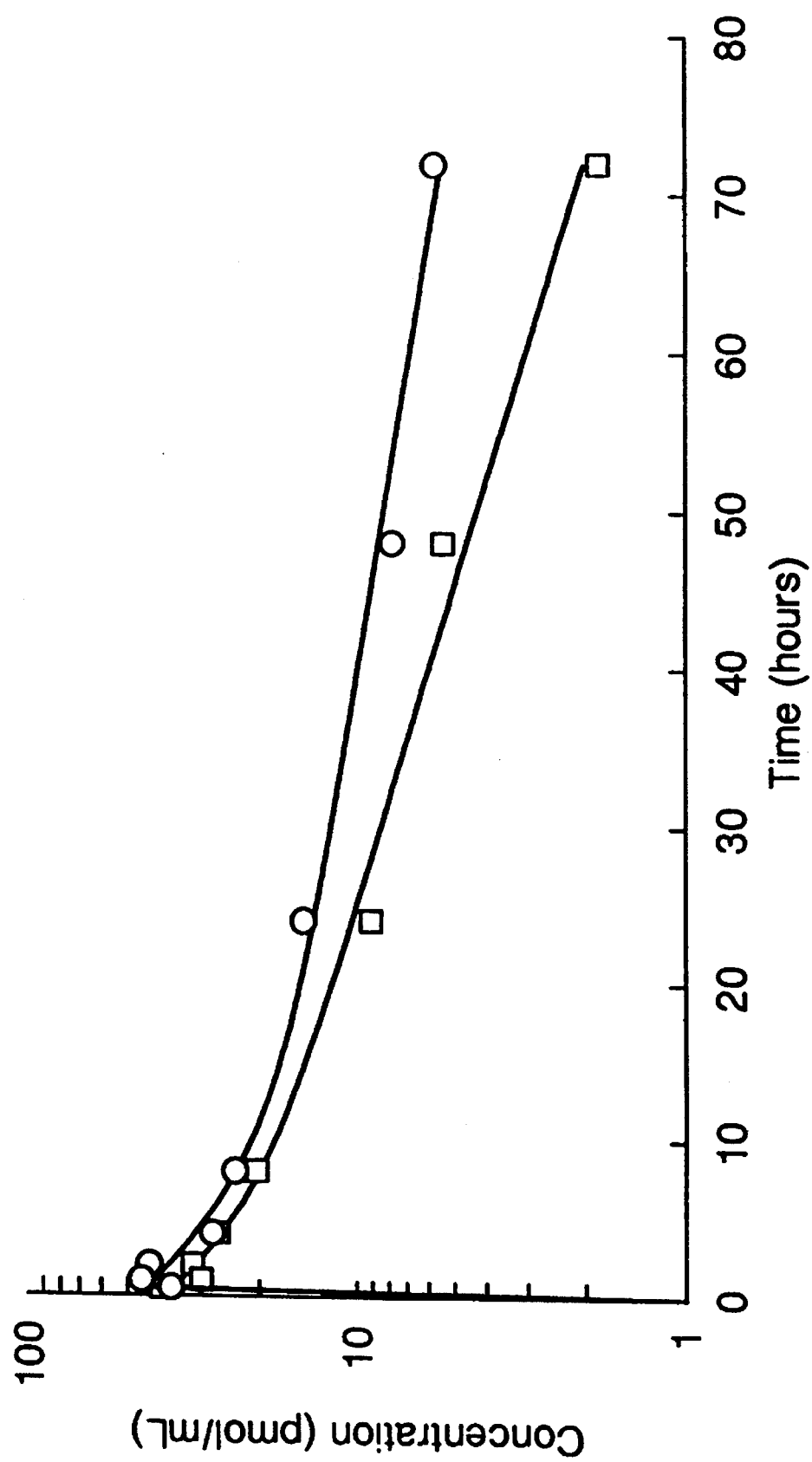

Furthermore, as depicted in FIG. 7B and Table 4, the immunoconjugate was cleared more rapidly from plasma, had a shorter elimination half-life, and had a larger volume of distribution in SCID mice with end-stage human B-lineage leukemia (i.e., SCID mice with disseminated human B-lineage leukemia paralyzed secondary to CNS involvement), when compared to its disposition in healthy SCID mice which have not been inoculated with leukemia cells. These differences suggest that B43-GEN immunoconjugate binds to CD19-positive leukemia cells infiltrating SCID mouse tissues, resulting in more rapid removal of the immunoconjugate from plasma in mice with end-stage leukemia.

Figure 7C:
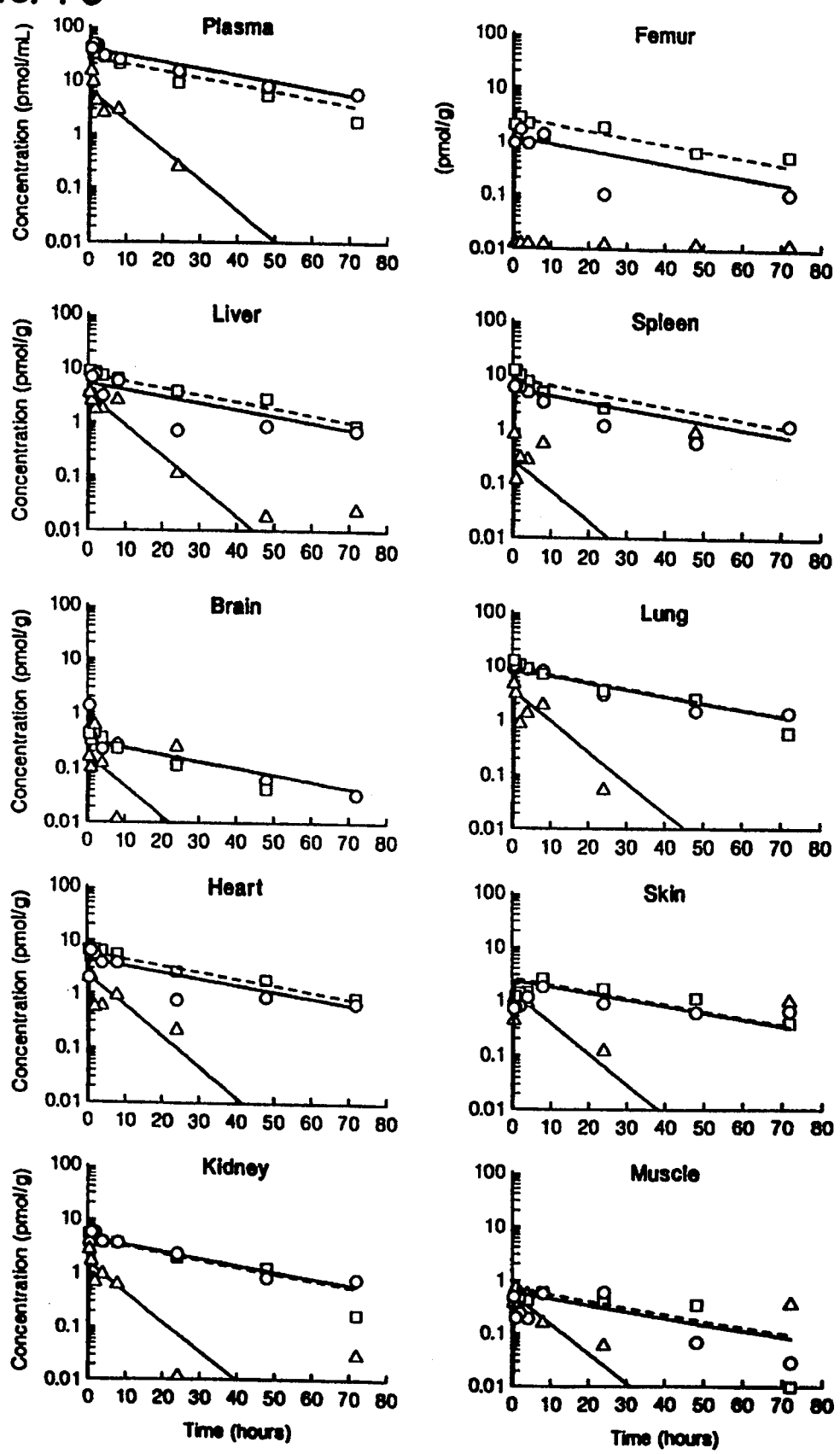

This hypothesis is supported by measurement of higher concentrations of the immunoconjugate in tissues of SCID mice with end-stage leukemia, when compared to healthy SCID mice which have not been inoculated with leukemia cells (FIG. 7C). The spleen, liver, and lungs had the highest tissue-to-plasma ratio, with the tissue distribution ratio increasing approximately 2-fold in spleen and liver of mice with end-stage leukemia (Table 5). Although tissue distribution of the immunoconjugate into the femur was low in mice with a minimal leukemia burden, it increased 3-fold in mice with end-stage leukemia, reflecting binding of the immunoconjugate to CD19 positive human B-lineage leukemia cells infiltrating bone marrow.

Furthermore, within one hour after injection of non-radioactive B43-GEN, the presence of B43-GEN molecules on the surface of leukemia cells infiltrating the bone marrow, liver, and spleen of SCID mice was confirmed by indirect immunofluorescence and flow cytometry using FITC labeled goat-anti-mouse IgG targeted against the B43 antibody moiety of the immunoconjugate. Lower tissue levels of unconjugated GEN indicate that it is cleared from the body more rapidly than B43-GEN immunoconjugate (FIG. 7C). The total systemic clearances of GEN and B43-GEN estimated by the physiological model (Table 5) were in close agreement with clearances estimated by the two-compartment operational model (Table 4).

Figure 8:
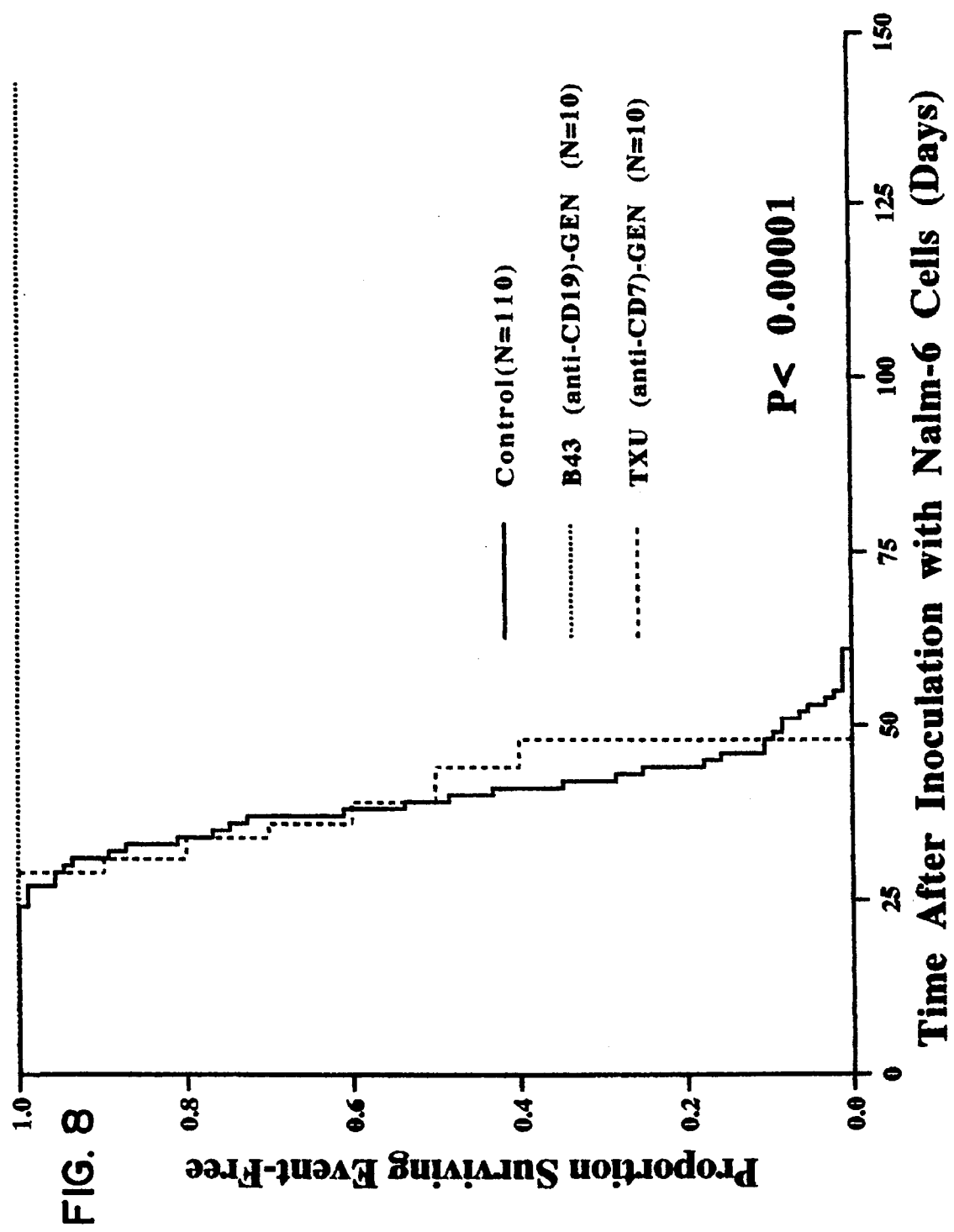
FIG. 8 is a graph depicting of the antileukemic activity of B43-GEN immunoconjugate against human B-lineage leukemia in SCID mice. The probability of event-free survival was determined and event-free interval curves were generated using the Kaplan-Meier product limit method.

The anti-leukemic activity of B43-GEN was also evaluated in SCID mice subjected to the identical pharmacological protocol as stated above. All control mice treated with unconjugated GEN, unconjugated B43 antibody, TXU(anti-CD7)-GEN control immunoconjugate, or PBS died of disseminated human B-lineage leukemia at 24 to 61 days after inoculation (FIG. 8). In contrast, all mice treated with B43-GEN immunoconjugate at either 25 μg/mouse or 50 μg/mouse=335 pmols/mouse remained alive without clinical evidence of leukemia for >4 months. These long-term surviving mice were electively killed at 142 days in order to examine their burden of human leukemia cells. Post-mortem histopathologic examination of tissue sections from multiple organs did not reveal any leukemic infiltrates. Furthermore, we found no molecular evidence of occult leukemia when DNA from bone marrow, spleen, liver, and brain/meninges was examined for human μ-globin gene sequences by PCR (FIG. 9).

Figure 9:
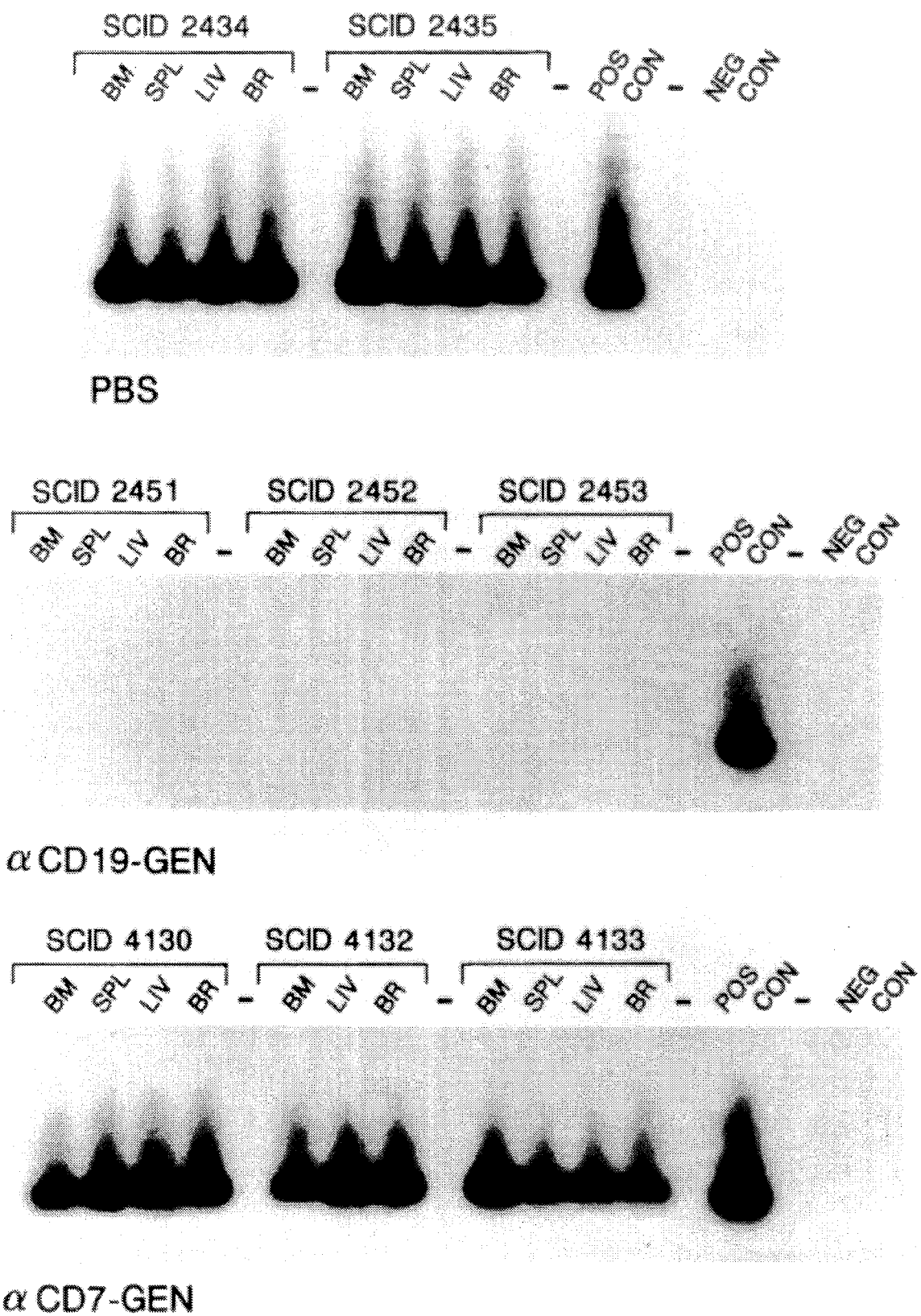
FIG. 9 is a depiction of the PCR analysis of SCID mouse organs from B43-GEN treated long-term survivors for human B-lineage leukemia cells.

By comparison, diffuse leukemic infiltrates as well as PCR evidence of human DNA were found in bone marrow, liver, spleen, and meninges of SCID mice treated with PBS or TXU(anti-CD7)-GEN (FIG. 9). We have previously reported that the injection of a single NALM-6 cell will cause disseminated fatal leukemia in SCID mice. Uckun et al., *Blood*, 79, 2201 (1992). The absence of engrafted leukemia cells in B43-GEN treated SCID mice 20 weeks after inoculation of 1×10⁶ NALM-6 cells indicates that at non-toxic dose levels this immunoconjugate killed >99.999% of NALM-6 cells in vivo.

B43-GEN was not toxic to SCID mice at doses ranging from 10 μg (67 pmols) to 250 μg (1667 pmols). None of the 42 mice treated with B43-GEN experienced side effects or died of toxicity during the 36 day observation period. No histopathologic lesions were found in the organs of B43-GEN treated mice that were electively killed at 36–37 days. Thus, the maximum tolerated dose (MTD) of B43-GEN was not reached at 250 μg/mouse (or 12.5 mg/kg).

TABLE 6

Anti-leukemic Activity of B43 (anti-CD-19)-GEN Immunoconjugate
Against Human B-lineage Leukemia in SCID Mice

| Treatment Group | Schedule | Number of Mice | EFS (%) 60 days | EFS (%) 120 days | Median EFS (Days) | P-value (vs B43-GEN) |
|---|---|---|---|---|---|---|
| Control | See the legend | 110 | 1 | 0 | 39 | <0.001 |
| PTK Inhibitors | | | | | | |
| B43 (anti-CD19)-GEM | 12.5/25 mg/m²/d × 3 d | 10 | 100 | 100 | >120 | — |
| TXU (anti-CD7)-GEN | 25 mg/m²/d × 3 d | 10 | 0 | 0 | 44 | <0.00001 |
| B43 (anti-CD19)-DIAI | 12.5/25 mg/m²/d × 3 d | 10 | 60 | 20 | 81 | <0.00001 |
| Alkylating Agents | | | | | | |
| Cyclophosphamide | 300 mg/m²/d × 10 d | 10 | 40 | 10 | 54 | <0.00001 |
| Carmustine | 150 mg/m² × 1 | 5 | 20 | 0 | 54 | <0.00001 |
| Topoisomerase Inhibitors | | | | | | |
| Etoposide | 1.7 mg/m² × 1 | 10 | 60 | 30 | 66 | <0.00001 |
| Topotecan | 150 mg/m²/72 h | 10 | 18 | 0 | 44 | <0.00001 |
| Antimetabolites | | | | | | |
| Cytarabine | 300 mg/m²/d × 10 d | 5 | 20 | 0 | 57 | <0.00001 |
| Mitotic Inhibitors | | | | | | |
| Taxol | 60 mg/m²/d × 5 d | 10 | 0 | 0 | 37 | <0.00001 |
| Vincristine | 30 mg/m² qwk × 4 | 5 | 0 | 0 | 51 | <0.00001 |
| Immunotoxins | | | | | | |
| B43 (anti-CD19)-PAP | 10 mg/m²/d × 3 d | 20 | 90 | 55 | >120 | <0.01 |
| J3-109 (anti-CD72-PAP | 15 mg/m²/d × 3 d | 10 | 20 | 0 | 51 | <0.00001 |
| Other Agents | | | | | | |
| Methylprednisone | 30 mg/m²/d × 10 d | 10 | 40 | 20 | 56 | <0.00001 |
| Doxorubicin | 6 mg/m²/d × 10 d | 5 | 20 | 0 | 49 | <0.00001 |
| L-asparaginase | 30,000 IU/m² qod × 5 | 5 | 0 | 0 | 44 | <0.00001 |
| TBI | 2.5 Gy → BMT | 5 | 0 | 0 | 47 | <0.00001 |

As shown in Table 6, similar levels of therapeutic efficacy could not be achieved by standard or investigational chemotherapeutic agents, including the alkylating agents cyclophosphamide and carmustine, the topoisomerase II inhibitor etoposide, the topoisomerase I inhibitor topotecan, the antimetabolite cytarabine, mitotic inhibitors taxol and vincristine, pokeweed antiviral protein (PAP) immunotoxins directed against CD19 or CD72 pan-B cell antigens, methylprednisone, doxorubicin, L-asparaginase, or 250 cGy total body irradiation. Another PTK inhibitory anti-CD19 immunoconjugate containing the genistein analogue daidzein (DAI), which is a less potent PTK inhibitor than GEN, although effective, was not as potent as B43-GEN (Table 6).

All publications, patents and patent documents are incorporated by reference herein, as though individually incorporated by reference. The invention has been described with reference to specific and preferred embodiments and techniques. However, it should be understood that many variations and modifications may be made while remaining within the spirit and scope of the invention.

What is claimed is:

1. An immunoconjugate comprising genistein linked to an anti-CD19 antibody which specifically binds to cell surface CD19 receptor, wherein said immunoconjugate inhibits CD19 associated tyrosine kinase, thereby inducing apoptosis and cell death.

2. The immunoconjugate of claim 1, wherein the genistein is linked to the antibody by photoaffinity cross-linking.

3. The immunoconjugate of claim 1, wherein the anti-CD19 antibody is B43 produced by hybridoma cells having ATCC accession number HB 8903 or a CD19 specific antibody derived from B43.

4. An immunoconjugate comprising genistein linked to an antibody produced by hybridoma cells having ATCC accession number HB 8903.

* * * * *

UNITED STATES PATENT AND TRADEMARK OFFICE
CERTIFICATE OF CORRECTION

PATENT NO. : 5,587,459

DATED : 24 Dec. 1996

INVENTOR(S) : Uckun

It is certified that error appears in the above-identified patent and that said Letters Patent is hereby corrected as shown below:

In column 9, line 13-14, delete "12301 Parklawn Dr." after the letters "(ATCC),"; line 14, delete "20852" after the word "Md.".

In column 10, line 12, "il" should read --$\beta$--.

In column 11, line 13, "REACTI-VIALS" should read --used--.

In column 12, line 41, "Reacti-Vials" should read --REACTI-VIALS--.

In column 14, line 1, "femtomlo" should read --femtomoles--. line 2, "108" should read --$10^8$--; table 3, line 5, "Fentomoles" should read --Femtomoles--.

In column 15, line 49, "Kinase" should read --kinase--.

In column 20, line 41, "µ-globin" should read --$\beta$-globin--.

Signed and Sealed this

Eighteenth Day of November 1997

BRUCE LEHMAN

*Attest:*

*Attesting Officer*   *Commissioner of Patents and Trademarks*